(12) United States Patent
Schulte et al.

(10) Patent No.: US 8,168,556 B2
(45) Date of Patent: May 1, 2012

(54) RACEMOSELECTIVE SYNTHESIS OF ANSA-METALLOCENE COMPOUNDS, ANSA-METALLOCENE COMPOUNDS, CATALYSTS COMPRISING THEM, PROCESS FOR PRODUCING AN OLEFIN POLYMER BY USE OF THE CATALYSTS, AND OLEFIN HOMO- AND COPOLYMERS

(75) Inventors: Joerg Schulte, Frankfurt (DE); Thorsten Sell, Worms (DE); Matthew Grant Thorn, Lebanon, OH (US); Andreas Winter, Neuleiningen (DE); Anita Dimeska, Bad Durkheim (DE)

(73) Assignee: Lummus Novolen Technology GmbH, Mannheim (DE)

( * ) Notice: Subject to any disclaimer, the term of this patent is extended or adjusted under 35 U.S.C. 154(b) by 99 days.

(21) Appl. No.: 12/739,347

(22) PCT Filed: Oct. 25, 2007

(86) PCT No.: PCT/US2007/022613
§ 371 (c)(1),
(2), (4) Date: Apr. 22, 2010

(87) PCT Pub. No.: WO2009/054831
PCT Pub. Date: Apr. 30, 2009

(65) Prior Publication Data
US 2010/0261860 A1  Oct. 14, 2010

(51) Int. Cl.
C08F 4/6592 (2006.01)
B01J 31/22 (2006.01)
C07F 17/00 (2006.01)

(52) U.S. Cl. ........ 502/152; 502/103; 502/104; 526/133; 526/134; 526/160; 526/165; 526/348; 526/943

(58) Field of Classification Search ............... 556/53; 502/103, 104, 152; 526/133, 134, 160, 165, 526/348, 943
See application file for complete search history.

(56) References Cited

U.S. PATENT DOCUMENTS

| | | | |
|---|---|---|---|
| 5,304,614 A | 4/1994 | Winter et al. | |
| 6,380,334 B1 | 4/2002 | Kuchta et al. | |
| 6,433,203 B1 * | 8/2002 | Dall'occo et al. | 556/11 |
| 6,465,384 B1 * | 10/2002 | Timmers et al. | 502/152 |
| 7,342,078 B2 | 3/2008 | Schottek et al. | |

FOREIGN PATENT DOCUMENTS

| | | |
|---|---|---|
| DE | 196 06 167 A1 | 8/1997 |
| DE | 196 22 207 A1 | 12/1997 |
| DE | 198 04 970 A1 | 8/1999 |
| DE | 100 30 638 A1 | 1/2002 |

(Continued)

OTHER PUBLICATIONS

International Search Report from PCT/US2007/022613 dated Jul. 24, 2008 (3 pages).

(Continued)

*Primary Examiner* — Caixia Lu
(74) *Attorney, Agent, or Firm* — Osha • Liang LLP

(57) ABSTRACT

A metallocene compound with the 4- and 7-positions on the indenyl moiety possessing large aromatic substituents is prepared in accordance with a method which produces substantially 100 percent racemic isomer. Advantageously, polymerization catalysts including the metallocene of the invention provide superior olefin polymerization results.

27 Claims, 2 Drawing Sheets

FOREIGN PATENT DOCUMENTS

| | | |
|---|---|---|
| EP | 0 302 424 A1 | 2/1989 |
| EP | 0 601 830 A2 | 6/1994 |
| EP | 0 811 627 A2 | 12/1997 |
| EP | 0 824 112 A1 | 2/1998 |
| EP | 0 824 113 A1 | 2/1998 |
| EP | 0 924 223 A2 | 6/1999 |
| EP | 1 209 165 A2 | 5/2002 |
| WO | 94/28034 A1 | 12/1994 |
| WO | 97/11775 A1 | 4/1997 |
| WO | 98/01481 A1 | 1/1998 |
| WO | 99/06414 A1 | 2/1999 |
| WO | 99/15538 A1 | 4/1999 |
| WO | 00/05277 A1 | 2/2000 |
| WO | 02/18397 A1 | 3/2002 |
| WO | 2004/037840 A1 | 5/2004 |
| WO | 2006/060544 A1 | 6/2006 |

OTHER PUBLICATIONS

Written Opinion from PCT/US2007/022613 dated Jul. 24, 2008 (5 pages).

Official Action issued May 26, 2011 in corresponding Russian application No. 2010120915 (11 pages).

Written Opinion and Search Report mailed Aug. 25, 2011 in corresponding Singapore Patent Application No. 201002932-0 (19 pages).

* cited by examiner

1

RACEMOSELECTIVE SYNTHESIS OF ANSA-METALLOCENE COMPOUNDS, ANSA-METALLOCENE COMPOUNDS, CATALYSTS COMPRISING THEM, PROCESS FOR PRODUCING AN OLEFIN POLYMER BY USE OF THE CATALYSTS, AND OLEFIN HOMO- AND COPOLYMERS

BACKGROUND

1. Field of the Invention

The present invention relates to a novel racemoselective synthesis of ansa-metallocene compounds, novel ansa-metallocene compounds useful as components in polymerization catalysts, a process for the polymerization of olefins, particularly propylene, and olefin homopolymers, random and impact copolymers prepared by using the metallocene catalysts.

2. Background of the Art

Chiral ansa-metallocenes of transition metals of the groups three to six of the Periodic Table of Elements are increasingly being used as components for the stereospecific polymerization of olefins. For example, bridged substituted bis(indenyl) zirconium dichlorides are among the most important class of catalyst components for the manufacturing of isotactic polypropylene [Brintzinger, H. H.; Fischer, D.; Mühlhaupt, R.; Rieger, B.; Waymouth, R. M. Angew. Chem., Int. Ed. Engl. 1995, 34, 1143./Resconi, L.; Cavallo, L.; Fait, A.; Piemontesi, F. Chem. Rev. 2000, 100, 1253/Pasquini, N. (Editor), Polypropylene Handbook, $2^{nd}$ Ed. 2005, Carl-Hanser Verlag München]. Appropriately substituted ansa-metallocene complexes for the generation of isotactic polypropylene are generally obtained as mixtures of the racemic form and the undesired meso form from the processes of the prior art.

The classical synthesis of ansa-metallocenes to the prior art generally involves the deprotonation of a bis-indenyl-ligand by a strong base, followed by the reaction with zirconium tetrachloride or its solvent adducts. This classical path has two substantial drawbacks. Instead of the desired racemate, almost equivalent amounts of the mirror-symmetric meso diastereomer are formed in most cases. The meso isomer has to be removed from the mixture, either by means of destruction of the meso form, or removal by crystallization steps. The separation procedure generally lowers the yield of the amount of possible pure racemic complex. The other drawback is the low solubility of metallocene complexes, which leads to the use of large amounts of solvents for the final separation of the racemic and meso forms.

Several, so called "racemoselective" syntheses were described in the literature [see LoCoco, M. D.; Zhang, X.; Jordan, R. F., *J. Am. Chem. Soc.* 2004; 126 (46); 15231-15244 and cited lit.], comprising the use of alternative zirconium sources, which have to be synthesized prior to the manufacturing of the metallocene. WO2004/037840, WO99/15538 and DE10030638 describe multistage processes for preparing racemic metallocene complexes via biphenoxide- or bisphenoxide-substituted metallocenes as intermediates. These approaches lead to metallocenes substituted at zirconium with oxide or amide moieties. These intermediates have to be converted to the corresponding dichlorides in order to use them as catalyst components, thus adding extra steps to the synthesis.

U.S. Pat. No. 5,304,614 describes 2,4,7-substituted trialkyl-substituted metallocenes, which were obtained as mixtures between the racemic and the meso forms.

It is an object of this invention to provide novel ansa-metallocene structures for the selective preparation of the racemic complexes, which are virtually free of the meso isomer. Not to be bound by any particular theory, the inventors postulate that in order to achieve an intrinsic racemoselectivity, the hindrance of the formation of the meso form might be achieved by steric hindrance of the formation of the meso form. Attaching two large aromatic substituents to the indenyl-moiety in the 4- and in the 7-position should hinder the formation of the meso-form of the complexes. FIG. 1 illustrates this concept.

Another object of the present invention is to address the shortcoming of the state of the art metallocene compounds to provide metallocenes that afford high melting point, high molar mass homopolymers and high molar mass copolymers at high productivities when used as components of supported catalysts under industrially relevant polymerization conditions at temperatures of from 50° C. to 100° C.

Another objective of the present invention is to provide a process for the polymerization of olefins, particularly propylene, ethylene, and optionally one or more higher 1-olefins.

Furthermore, it is an objective of the present invention to provide olefin polymers, particularly propylene homopolymers, random copolymers of propylene with ethylene and/or higher 1-olefins, impact copolymers comprised of propylene, ethylene and/or optionally higher 1-olefins, and random impact copolymers comprised of propylene, ethylene and/or optionally higher 1-olefins.

SUMMARY OF THE INVENTION

A metallocene compound having formula 1 below is provided herein, wherein the 4- and 7-positions (corresponding to the substituents $R^5$ and $R^8$, respectively) on the indenyl moiety possess large aromatic substituents. The metallocene compound is prepared in accordance with a method which produces substantially pure racemic isomer. Advantageously, polymerisation catalysts comprising the metallocene of the invention provide superior olefin polymerisation results.

BRIEF DESCRIPTION OF THE DRAWINGS

Various embodiments are described below with reference to the drawings wherein.

DETAILED DESCRIPTION OF THE PREFERRED EMBODIMENT(S)

Figure 1:
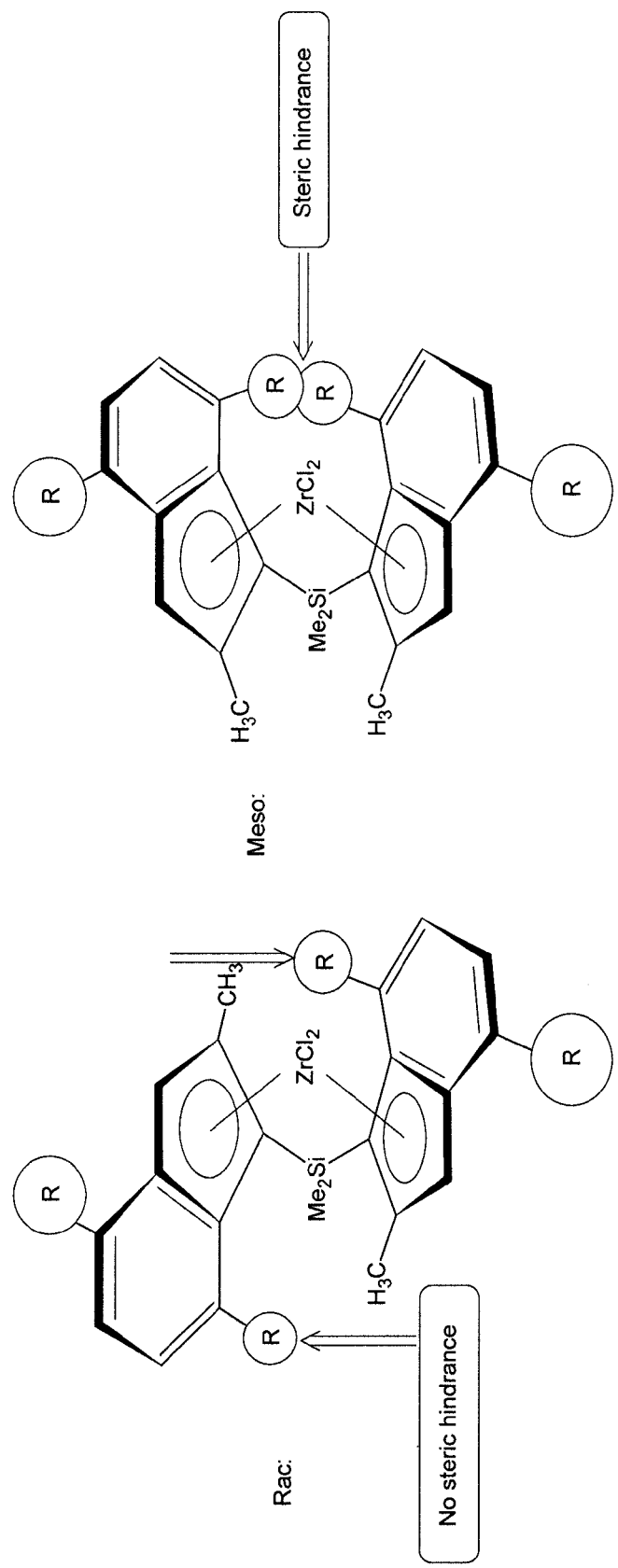
FIG. 1 is a diagrammatic illustration of the steric effects of attaching two large aromatic substituents in the 4- and 7-positions of the indenyl moiety (corresponding to the substituents $R^5$ and $R^8$, respectively, in formula 1)

Surprisingly it was found that bridged bis-indenyl ligands with a special substitution pattern lead selectively to racemic ansa-metallocenes. Particularly, as shown in FIG. 1, when the 4- and 7-positions on the indenyl moiety (corresponding to the substituents $R^5$ and $R^8$, respectively) possess large aromatic constituents the affects of steric hinderance prevent the formation of the meso isomer of the metallocene. Instead, the product of the method of the present invention is substantially pure racemic isomer as synthesized without any need for further separation processes. By "substantially pure" is meant at least 90% racemic isomer, preferably at least 95% racemic isomer, and more preferably at least 99% racemic isomer.

The first embodiment of the invention relates to a specifically substituted, bridged metallocene component of the general Formula 1 below:

Formula 1

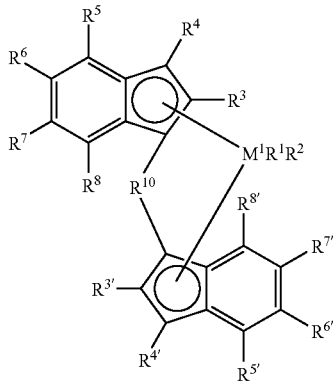

in which:

$M^1$ is a metal of the Groups 4-6 of the Periodic Table of the Elements, $R^1$ and $R^2$ are identical or different and are each a hydrogen atom, an alkyl group of from 1 to about 10 carbon atoms, an alkoxy group of from 1 to about 10 carbon atoms, an aryl group of from 6 to about 20 carbon atoms, an aryloxy group of from 6 to about 10 carbon atoms, an alkenyl group of from 2 to about 10 carbon atoms, an OH group, a halogen atom, or a $NR_2^{32}$ group, where $R^{32}$ is an alkyl group of from 1 to about 10 carbon atoms or an aryl group of from 6 to about 14 carbon atoms and $R^1$ and $R^2$ may form one or more ring system(s).

$R^3$ and $R^{3'}$ are identical or different and are each a hydrogen atom, a linear, cyclic or branched hydrocarbon group which may be halogenated and/or may contain one or more hetero atoms like Si, B, Al, O, S, N or P, for example an alkyl group of from 1 to about 20 carbon atoms, an alkylalkenyl group of from 3 to about 20 carbon atoms, an alkylaryl group of from 7 to about 40 carbon atoms, or an alkylarylalkenyl group of from 9 to about 40 carbon atoms, an arylalkyl group of 7 to 20 carbon atoms, an alkoxy group of from 1 to about 10 carbon atoms, an aryl group of from 6 to about 20 carbon atoms, a heteroaryl group of 3 to about 20 carbon atoms, an aryloxy group of from 6 to about 10 carbon atoms, a silyloxy group of about 3 to 20 carbon atoms, an alkenyl group of from 2 to about 10 carbon atoms, a halogen atom, or a $NR_2^{32}$ group, where $R^{32}$ is an alkyl group of from 1 to about 10 carbon atoms or an aryl group of from 6 to about 14 carbon atoms, $R^4$ and $R^{4'}$ are identical or different and are each a hydrogen atom, a linear, cyclic or branched hydrocarbon group which may be halogenated and/or may contain one or more hetero atoms like Si, B, Al, O, S, N or P, for example an alkyl group of from 1 to about 20 carbon atoms, an alkylalkenyl group of from 3 to about 20 carbon atoms, an alkylaryl group of from 7 to about 40 carbon atoms, or an alkylarylalkenyl group of from 9 to about 40 carbon atoms, an arylalkyl group of 7 to 20 carbon atoms, an alkoxy group of from 1 to about 10 carbon atoms, an aryl group of from 6 to about 20 carbon atoms, a heteroaryl group of 3 to about 20 carbon atoms, an aryloxy group of from 6 to about 10 carbon atoms, a silyloxy group of about 3 to 20 carbon atoms, an alkenyl group of from 2 to about 10 carbon atoms, a halogen atom, or a $NR_2^{32}$ group, where $R^{32}$ is an alkyl group of from 1 to about 10 carbon atoms or an aryl group of from 6 to about 14 carbon atoms, $R^5$, $R^{5'}$, $R^8$ and $R^{8'}$ are identical or different and are each an aryl group of from 6 to about 40 carbon atoms, an alkylaryl group of from 7 to about 40 carbon atoms, or an alkenylaryl group of from 8 to about 40 carbon atoms or a substituted or unsubstituted silylaryl group, or an (alkyl)(silyl)aryl group. The groups may contain one or more hetero atoms like Si, B, Al, O, S, N or P, and/or may contain halogen atoms like F, Cl or Br, $R^6$, $R^{6'}$, $R^7$ and $R^{7'}$ are identical or different and are each a hydrogen atom, a linear, cyclic or branched hydrocarbon group which may be halogenated and/or may contain one or more hetero atoms like Si, B, Al, O, S, N or P, for example an alkyl group of from 1 to about 20 carbon atoms, an alkylalkenyl group of from 3 to about 20 carbon atoms, an alkylaryl group of from 7 to about 40 carbon atoms, or an alkylarylalkenyl group of from 9 to about 40 carbon atoms, an arylalkyl group of 7 to 20 carbon atoms, an alkoxy group of from 1 to about 10 carbon atoms, an aryl group of from 6 to about 20 carbon atoms, a heteroaryl group of 3 to about 20 carbon atoms, an aryloxy group of from 6 to about 10 carbon atoms, a silyloxy group of about 3 to 20 carbon atoms, an alkenyl group of from 2 to about 10 carbon atoms, a halogen atom, or a $NR_2^{32}$ group, where $R^{32}$ is an alkyl group of from 1 to about 10 carbon atoms or an aryl group of from 6 to about 14 carbon atoms, $R^{10}$ is a bridging group wherein $R^{10}$ is selected from:

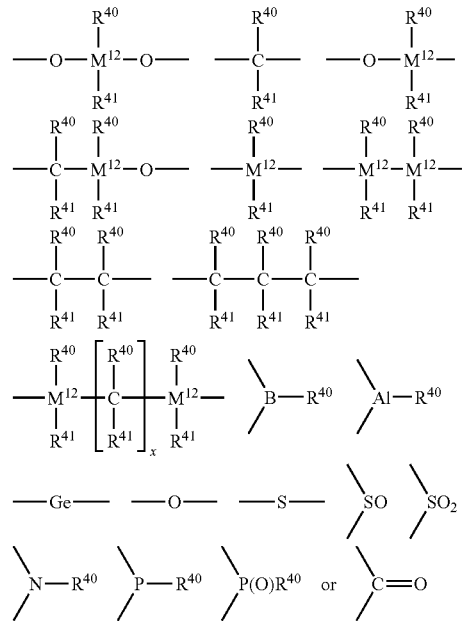

where $R^{40}$ and $R^{41}$, even when bearing the same index, can be identical or different and are each a hydrogen atom, a $C_1$-$C_{40}$ group such as an alkyl group having from 1 to about 30 carbon atoms, an aryl group of from 6 to about 40 carbon atoms, a fluoroalkyl group of from 1 to about 10 carbon atoms, an alkoxy group of from 1 to about 10 carbon atoms, an aryloxy group of from 6 to about 10 carbon atoms, an alkenyl group of from 2 to about 10 carbon atoms, an arylalkyl group of from 7 to about 40 carbon atoms, an alkylaryl group of from 7 to about 40 carbon atoms, a substituted or unsubstituted alkylsilyl, alkyl(aryl)silyl or arylsilyl group or an arylalkenyl group of from 8 to about 40 carbon atoms. $R^{40}$ and $R^{41}$ together with the atoms connecting them can form one or more cyclic systems or $R^{40}$ and/or $R^{41}$ can contain additional hetero atoms (i.e., non-carbon atoms) like Si, B, Al, O, S, N or P or halogen atoms like Cl or Br, x is an integer from 1 to 18, $M^{12}$ is silicon, germanium or tin, and $R^{10}$ may also link two units of the formula 1 to one another.

Preferred are compounds of the formula 1 in which $M^1$ is a metal of the Group 4 of the Periodic Table of the Elements, $R^1$ and $R^2$ are identical or different and are each an alkyl group of from 1 to about 10 carbon atoms, an alkoxy group of from 1 to about 10 carbon atoms, an aryloxy group of from 6 to about 10 carbon atoms or a halogen atom, or $R^1$ and $R^2$ together may form one or more ring system(s), $R^3$ and $R^{3'}$ are identical or different and are each a linear, cyclic or branched hydrocarbon group which may be halogenated and/or may contain one or more hetero atoms like Si, B, Al, O, S, N or P, for example an alkyl group of from 1 to about 10 carbon atoms, an alkylalkenyl group of from 3 to about 10 carbon atoms, an alkylaryl group of from 7 to about 20 carbon atoms, or an alkylarylalkenyl group of from 9 to about 20 carbon atoms, an arylalkyl group of 7 to 15 carbon atoms, an alkoxy group of from 1 to about 6 carbon atoms, an aryl group of from 6 to about 10 carbon atoms, a heteroaryl group of 3 to about 10 carbon atoms, an aryloxy group of from 6 to about 10 carbon atoms, a silyloxy group of about 3 to 10 carbon atoms, an alkenyl group of from 2 to about 6 carbon atoms, a halogen atom, or a $NR_2^{32}$ group, where $R^{32}$ is an alkyl group of from 1 to about 10 carbon atoms or an aryl group of from 6 to about 10 carbon atoms.

$R^4$ and $R^{4'}$ are identical or different and are each a hydrogen atom, a linear, cyclic or branched hydrocarbon group which may be halogenated and/or may contain one or more hetero atoms like Si, B, Al, O, S, N or P, for example an alkyl group of from 1 to about 20 carbon atoms, $R^5$, $R^{5'}$, $R^8$ and $R^{8'}$ are identical or different and are each an aryl group of from 6 to about 40 carbon atoms, an alkylaryl group of from 7 to about 40 carbon atoms. The groups may contain one or more hetero atoms like B, Al, O, S, N or P, and/or may contain halogen atoms like F, Cl or Br.

$R^6$, $R^{6'}$, $R^7$ and $R^{7'}$ are identical or different and are each a hydrogen atom, a linear, cyclic or branched hydrocarbon group which may be halogenated and/or may contain one or more hetero atoms like B, Al, O, S, N or P, for example an alkyl group of from 1 to about 20 carbon atoms.

$R^{10}$ is $R^{40}R^{41}Si=$, $R^{40}R^{41}Ge=$, $R^{40}R^{41}C=$ or $-(R^{40}R^{41}C-CR^{40}R^{41})-$, where $R^{40}$ and $R^{41}$ are identical or different and are each a hydrogen atom, a hydrocarbon group of from 1 to about 30 carbon atoms, in particular an alkyl group of from 1 to about 10 carbon atoms, an aryl group of from 6 to about 40 carbon atoms, an arylalkyl group of from 7 to about 14 carbon atoms, an alkylaryl group of from 7 to about 14 carbon atoms, Particularly preferred are compounds of the formula 1 in which $M^1$ is Zirconium, $R^1$ and $R^2$ are identical and are methyl, chlorine or phenolate, $R^3$ and $R^{3'}$ are identical and are a linear, cyclic or branched alkyl group like methyl, ethyl, n-propyl, i-propyl, cyclopropyl, n-butyl, t-butyl, t-butyl-methyl, i-butyl, s-butyl, n-pentyl, n-hexyl, n-heptyl, n-octyl, n-nonyl, n-decyl, cyclopropyl-methyl, cyclopentyl, cyclopentyl-methyl, cyclohexyl, cyclohexyl-methyl, (1-adamantyl)methyl, (2-adamantyl)methyl, or an arylalkyl group of 7 to 15 carbon atoms like benzyl, phenethyl or phenyl-propyl, $R^4$ and $R^{4'}$ are identical and are each a hydrogen atom, $R^5$, $R^{5'}$, $R^8$ and $R^{8'}$ are identical and are each an aryl group of from 6 to about 20 carbon atoms, like phenyl, 1-naphthyl, 2-naphtyl, an alkylaryl group of from 7 to about 40 carbon atoms which may contain one or more hetero atoms like B, Al, O, S, N or P, and/or may contain halogen atoms like F, Cl or Br, like 4-methyl-phenyl, 4-ethyl-phenyl, 4-i-propyl-phenyl, 4-t-butyl-phenyl, 3,5-dimethylphenyl, 3,5-di-t-butyl-4-methoxy-phenyl, 2,3,4,5,6-pentafluorophenyl, $R^6$, $R^{6'}$, $R^7$ and $R^{7'}$ are identical and are each a hydrogen atom. The bridging unit $R^{10}$ is $R^{40}R^{41}Si=$ or $R^{40}R^{41}Ge=$, where $R^{40}$ and $R^{41}$ are identical or different and are methyl, ethyl, propyl, butyl, pentyl, hexyl, heptyl, octyl, nonyl, decyl, undecyl, dodecyl, cyclopentyl, cyclopentadienyl, cyclohexyl, phenyl, naphthyl, benzyl or 3,3,3-trifluoropropyl.

Very particularly preferred are compounds of the formula 1 in which $M^1$ is Zirconium, $R^1$ and $R^2$ are identical and are methyl or chlorine, $R^3$ and $R^{3'}$ are identical and are a linear, cyclic or branched alkyl group like methyl, n-heptyl, n-octyl, n-nonyl, n-decyl, cyclohexyl-methyl, t-butyl-methyl, (2-adamantyl)methyl, (1-adamantyl)methyl, or an arylalkyl group of 7 to 15 carbon atoms like benzyl, phenethyl or phenyl-propyl, $R^4$ and $R^{4'}$ are identical and are each a hydrogen atom, $R^5$, $R^{5'}$, $R^8$ and $R^{8'}$ are identical and are each an aryl group of from 6 to about 20 carbon atoms, like phenyl, 1-naphthyl, 2-naphtyl, an alkylaryl group of from 7 to about 40 carbon atoms which may contain one or more hetero atoms like B, Al, O, S, N or P, and/or may contain halogen atoms like F, Cl or Br, like 4-methyl-phenyl, 4-ethyl-phenyl, 4-i-propyl-phenyl, 4-t-butyl-phenyl, 3,5-dimethylphenyl, 3,5-di-t-butyl-4-methoxy-phenyl, 2,3,4,5,6-pentafluorophenyl, $R^6$, $R^{6'}$, $R^7$ and $R^{7'}$ are identical and are each a hydrogen atom. The bridging unit $R^{10}$ is $R^{40}R^{41}Si=$ or $R^{40}R^{41}Ge=$, where $R^{40}$ and $R^{41}$ are identical or different and are methyl, ethyl, propyl, butyl, pentyl, hexyl, heptyl, octyl, nonyl, decyl, undecyl, dodecyl, cyclopentyl, cyclopentadienyl, cyclohexyl, phenyl, naphthyl, benzyl or 3,3,3-trifluoropropyl.

Non-limiting examples for the metallocene compounds according to Formula 1 are:

Dimethylsilanediylbis(2-methyl-4,7-diphenyl-indenyl)zirconium dichloride;

Dimethylsilanediylbis(2-ethyl-4,7-diphenyl-indenyl)zirconium dichloride;

Dimethylsilanediylbis(2-n-propyl-4,7-diphenyl-indenyl)zirconium dichloride;

Dimethylsilanediylbis(2-i-propyl-4,7-diphenyl-indenyl)zirconium dichloride;

Dimethylsilanediylbis(2-n-butyl-4,7-diphenyl-indenyl)zirconium dichloride;

Dimethylsilanediylbis(2-s-butyl-4,7-diphenyl-indenyl)zirconium dichloride;

Dimethylsilanediylbis(2-t-butyl-4,7-diphenyl-indenyl)zirconium dichloride;

Dimethylsilanediylbis(2-n-pentyl-4,7-diphenyl-indenyl)zirconium dichloride;

Dimethylsilanediylbis(2-n-hexyl-4,7-diphenyl-indenyl)zirconium dichloride;

Dimethylsilanediylbis(2-n-heptyl-4,7-diphenyl-indenyl)zirconium dichloride;

Dimethylsilanediylbis(2-cyclopropylmethyl-4,7-diphenyl-indenyl)zirconium dichloride;

Dimethylsilanediylbis(2-cyclobutylmethyl-4,7-diphenyl-indenyl)zirconium dichloride;

Dimethylsilanediylbis(2-cyclopentylmethyl-4,7-diphenyl-indenyl)zirconium dichloride;
Dimethylsilanediylbis(2-cyclohexylmethyl-4,7-diphenyl-indenyl)zirconium dichloride;
Dimethylsilanediylbis(2-cycloheptylmethyl-4,7-diphenyl-indenyl)zirconium dichloride;
Dimethylsilanediylbis(2-(1-adamantyl)methyl-4,7-diphenyl-indenyl)zirconium dichloride;
Dimethylsilanediylbis(2-t-butyl-methyl-4,7-diphenyl-indenyl)zirconium dichloride;
Dimethylsilanediylbis(2,4,7-triphenyl-indenyl)zirconium dichloride;
Dimethylsilanediylbis(2-benzyl-4,7-diphenyl-indenyl)zirconium dichloride;
Dimethylsilanediylbis(2-phenethyl-4,7-diphenyl-indenyl)zirconium dichloride;
Dimethylsilanediylbis(2-phenylpropyl-4,7-diphenyl-indenyl)zirconium dichloride;
Dimethylsilanediylbis(2-phenylbutyl-4,7-diphenyl-indenyl)zirconium dichloride;
Dimethylsilanediylbis(2-methyl-4,7-bis-(4-methyl-phenyl)-indenyl)zirconium dichloride;
Dimethylsilanediylbis(2-ethyl-4,7-bis-(4-methyl-phenyl)-indenyl)zirconium dichloride;
Dimethylsilanediylbis(2-n-propyl-4,7-bis-(4-methyl-phenyl)-indenyl)zirconium dichloride;
Dimethylsilanediylbis(2-i-propyl-4,7-bis-(4-methyl-phenyl)-indenyl)zirconium dichloride;
Dimethylsilanediylbis(2-n-butyl-4,7-bis-(4-methyl-phenyl)-indenyl)zirconium dichloride;
Dimethylsilanediylbis(2-s-butyl-4,7-bis-(4-methyl-phenyl)-indenyl)zirconium dichloride;
Dimethylsilanediylbis(2-t-butyl-4,7-bis-(4-methyl-phenyl)-indenyl)zirconium dichloride;
Dimethylsilanediylbis(2-n-pentyl-4,7-bis-(4-methyl-phenyl)-indenyl)zirconium dichloride;
Dimethylsilanediylbis(2-n-hexyl-4,7-bis-(4-methyl-phenyl)-indenyl)zirconium dichloride;
Dimethylsilanediylbis(2-n-heptyl-4,7-bis-(4-methyl-phenyl)-indenyl)zirconium dichloride;
Dimethylsilanediylbis(2-cyclopropylmethyl-4,7-bis-(4-methyl-phenyl)-indenyl)zirconium dichloride;
Dimethylsilanediylbis(2-cyclobutylmethyl-4,7-bis-(4-methyl-phenyl)-indenyl)zirconium dichloride;
Dimethylsilanediylbis(2-cyclopentylmethyl-4,7-bis-(4-methyl-phenyl)-indenyl)zirconium dichloride;
Dimethylsilanediylbis(2-cyclohexylmethyl-4,7-bis-(4-methyl-phenyl)-indenyl)zirconium dichloride;
Dimethylsilanediylbis(2-cycloheptylmethyl-4,7-bis-(4-methyl-phenyl)-indenyl)zirconium dichloride;
Dimethylsilanediylbis(2-(1-adamantyl)methyl-4,7-bis-(4-methyl-phenyl)-indenyl)zirconium dichloride;
Dimethylsilanediylbis(2-t-butyl-methyl-4,7-bis-(4-methyl-phenyl)-indenyl)zirconium dichloride;
Dimethylsilanediylbis(2-(1-furyl)-4,7-bis-(4-methyl-phenyl)-indenyl)zirconium dichloride;
Dimethylsilanediylbis(2-benzyl-4,7-bis-(4-methyl-phenyl)-indenyl)zirconium dichloride;
Dimethylsilanediylbis(2-phenethyl-4,7-bis-(4-methyl-phenyl)-indenyl)zirconium dichloride;
Dimethylsilanediylbis(2-phenylpropyl-4,7-bis-(4-methyl-phenyl)-indenyl)zirconium dichloride;
Dimethylsilanediylbis(2-phenylbutyl-4,7-bis-(4-methyl-phenyl)-indenyl)zirconium dichloride;
Dimethylsilanediylbis(2-methyl-4,7-bis-(4-t-butyl-phenyl)-indenyl)zirconium dichloride;
Dimethylsilanediylbis(2-ethyl-4,7-bis-(4-t-butyl-phenyl)-indenyl)zirconium dichloride;
Dimethylsilanediylbis(2-n-propyl-4,7-bis-(4-t-butyl-phenyl)-indenyl)zirconium dichloride;
Dimethylsilanediylbis(2-i-propyl-4,7-bis-(4-t-butyl-phenyl)-indenyl)zirconium dichloride;
Dimethylsilanediylbis(2-n-butyl-4,7-bis-(4-t-butyl-phenyl)-indenyl)zirconium dichloride;
Dimethylsilanediylbis(2-s-butyl-4,7-bis-(4-t-butyl-phenyl)-indenyl)zirconium dichloride;
Dimethylsilanediylbis(2-t-butyl-4,7-bis-(4-t-butyl-phenyl)-indenyl)zirconium dichloride;
Dimethylsilanediylbis(2-n-pentyl-4,7-bis-(4-t-butyl-phenyl)-indenyl)zirconium dichloride;
Dimethylsilanediylbis(2-n-hexyl-4,7-bis-(4-t-butyl-phenyl)-indenyl)zirconium dichloride;
Dimethylsilanediylbis(2-n-heptyl-4,7-bis-(4-t-butyl-phenyl)-indenyl)zirconium dichloride;
Dimethylsilanediylbis(2-cyclopropylmethyl-4,7-bis-(4-t-butyl-phenyl)-indenyl)zirconium dichloride;
Dimethylsilanediylbis(2-cyclobutylmethyl-4,7-bis-(4-t-butyl-phenyl)-indenyl)zirconium dichloride;
Dimethylsilanediylbis(2-cyclopentylmethyl-4,7-bis-(4-t-butyl-phenyl)-indenyl)zirconium dichloride;
Dimethylsilanediylbis(2-cyclohexylmethyl-4,7-bis-(4-t-butyl-phenyl)-indenyl)zirconium dichloride;
Dimethylsilanediylbis(2-cycloheptylmethyl-4,7-bis-(4-t-butyl-phenyl)-indenyl)zirconium dichloride;
Dimethylsilanediylbis(2-(1-adamantyl)methyl-4,7-bis-(4-t-butyl-phenyl)-indenyl)zirconium dichloride;
Dimethylsilanediylbis(2-t-butyl-methyl-4,7-bis-(4-t-butyl-phenyl)-indenyl)zirconium dichloride;
Dimethylsilanediylbis(2-(1-furyl)-4,7-bis-(4-t-butyl-phenyl)-indenyl)zirconium dichloride;
Dimethylsilanediylbis(2-benzyl-4,7-bis-(4-t-butyl-phenyl)-indenyl)zirconium dichloride;
Dimethylsilanediylbis(2-phenethyl-4,7-bis-(4-t-butyl-phenyl)-indenyl)zirconium dichloride;
Dimethylsilanediylbis(2-phenylpropyl-4,7-bis-(4-t-butyl-phenyl)-indenyl)zirconium dichloride;
Dimethylsilanediylbis(2-phenylbutyl-4,7-bis-(4-t-butyl-phenyl)-indenyl)zirconium dichloride;
Dimethylsilanediylbis(2-methyl-4,7-bis-(3,5-dimethyl-phenyl)-indenyl)zirconium dichloride;
Dimethylsilanediylbis(2-ethyl-4,7-bis-(3,5-dimethyl-phenyl)-indenyl)zirconium dichloride;
Dimethylsilanediylbis(2-n-propyl-4,7-bis-(3,5-dimethyl-phenyl)-indenyl)zirconium dichloride;
Dimethylsilanediylbis(2-i-propyl-4,7-bis-(3,5-dimethyl-phenyl)-indenyl)zirconium dichloride;
Dimethylsilanediylbis(2-n-butyl-4,7-bis-(3,5-dimethyl-phenyl)-indenyl)zirconium dichloride;
Dimethylsilanediylbis(2-s-butyl-4,7-bis-(3,5-dimethyl-phenyl)-indenyl)zirconium dichloride;
Dimethylsilanediylbis(2-t-butyl-4,7-bis-(3,5-dimethyl-phenyl)-indenyl)zirconium dichloride;
Dimethylsilanediylbis(2-n-pentyl-4,7-bis-(3,5-dimethyl-phenyl)-indenyl)zirconium dichloride;
Dimethylsilanediylbis(2-n-hexyl-4,7-bis-(3,5-dimethyl-phenyl)-indenyl)zirconium dichloride;
Dimethylsilanediylbis(2-n-heptyl-4,7-bis-(3,5-dimethyl-phenyl)-indenyl)zirconium dichloride;
Dimethylsilanediylbis(2-cyclopropylmethyl-4,7-bis-(3,5-dimethyl-phenyl)-indenyl)zirconium dichloride;
Dimethylsilanediylbis(2-cyclobutylmethyl-4,7-bis-(3,5-dimethyl-phenyl)-indenyl)zirconium dichloride;

Dimethylsilanediylbis(2-cyclopentylmethyl-4,7-bis-(3,5-dimethyl-phenyl)-indenyl)zirconium dichloride;
Dimethylsilanediylbis(2-cyclohexylmethyl-4,7-bis-(3,5-dimethyl-phenyl)-indenyl)zirconium dichloride;
Dimethylsilanediylbis(2-cycloheptylmethyl-4,7-bis-(3,5-dimethyl-phenyl)-indenyl)zirconium dichloride;
Dimethylsilanediylbis(2-(1-adamantyl)methyl-4,7-bis-(3,5-dimethyl-phenyl)-indenyl)zirconium dichloride;
Dimethylsilanediylbis(2-t-butyl-methyl-4,7-bis-(3,5-dimethyl-phenyl)-indenyl)zirconium dichloride;
Dimethylsilanediylbis(2-(1-furyl)-4,7-bis-(3,5-dimethyl-phenyl)-indenyl)zirconium dichloride;
Dimethylsilanediylbis(2-benzyl-4,7-bis-(3,5-dimethyl-phenyl)-indenyl)zirconium dichloride;
Dimethylsilanediylbis(2-phenethyl-4,7-bis-(3,5-dimethyl-phenyl)-indenyl)zirconium dichloride;
Dimethylsilanediylbis(2-phenylpropyl-4,7-bis-(3,5-dimethyl-phenyl)-indenyl)zirconium dichloride;
Dimethylsilanediylbis(2-phenylbutyl-4,7-bis-(3,5-dimethyl-phenyl)-indenyl)zirconium dichloride;
Dimethylsilanediylbis(2-methyl-4,7-bis-(1-naphthyl)-indenyl)zirconium dichloride;
Dimethylsilanediylbis(2-ethyl-4,7-bis-(1-naphthyl)-indenyl)zirconium dichloride;
Dimethylsilanediylbis(2-n-propyl-4,7-bis-(1-naphthyl)-indenyl)zirconium dichloride;
Dimethylsilanediylbis(2-i-propyl-4,7-bis-(1-naphthyl)-indenyl)zirconium dichloride;
Dimethylsilanediylbis(2-n-butyl-4,7-bis-(1-naphthyl)-indenyl)zirconium dichloride;
Dimethylsilanediylbis(2-s-butyl-4,7-bis-(1-naphthyl)-indenyl)zirconium dichloride;
Dimethylsilanediylbis(2-t-butyl-4,7-bis-(1-naphthyl)-indenyl)zirconium dichloride;
Dimethylsilanediylbis(2-n-pentyl-4,7-bis-(1-naphthyl)-indenyl)zirconium dichloride;
Dimethylsilanediylbis(2-n-hexyl-4,7-bis-(1-naphthyl)-indenyl)zirconium dichloride;
Dimethylsilanediylbis(2-n-heptyl-4,7-bis-(1-naphthyl)-indenyl)zirconium dichloride;
Dimethylsilanediylbis(2-cyclopropylmethyl-4,7-bis-(1-naphthyl)-indenyl)zirconium dichloride;
Dimethylsilanediylbis(2-cyclobutylmethyl-4,7-bis-(1-naphthyl)-indenyl)zirconium dichloride;
Dimethylsilanediylbis(2-cyclopentylmethyl-4,7-bis-(1-naphthyl)-indenyl)zirconium dichloride;
Dimethylsilanediylbis(2-cyclohexylmethyl-4,7-bis-(1-naphthyl)-indenyl)zirconium dichloride;
Dimethylsilanediylbis(2-cycloheptylmethyl-4,7-bis-(1-naphthyl)-indenyl)zirconium dichloride;
Dimethylsilanediylbis(2-(1-adamantyl)methyl-4,7-bis-(1-naphthyl)-indenyl)zirconium dichloride;
Dimethylsilanediylbis(2-t-butyl-methyl-4,7-bis-(1-naphthyl)-indenyl)zirconium dichloride;
Dimethylsilanediylbis(2-(1-furyl)-4,7-bis-(1-naphthyl)-indenyl)zirconium dichloride;
Dimethylsilanediylbis(2-benzyl-4,7-bis-(1-naphthyl)-indenyl)zirconium dichloride;
Dimethylsilanediylbis(2-phenethyl-4,7-bis-(1-naphthyl)-indenyl)zirconium dichloride;
Dimethylsilanediylbis(2-phenylpropyl-4,7-bis-(1-naphthyl)-indenyl)zirconium dichloride;
Dimethylsilanediylbis(2-phenylbutyl-4,7-bis-(1-naphthyl)-indenyl)zirconium dichloride;
Dimethylsilanediylbis(2-methyl-4,7-bis-(9-anthracenyl)-indenyl)zirconium dichloride;
Dimethylsilanediylbis(2-ethyl-4,7-bis-(9-anthracenyl)-indenyl)zirconium dichloride;
Dimethylsilanediylbis(2-n-propyl-4,7-bis-(9-anthracenyl)-indenyl)zirconium dichloride;
Dimethylsilanediylbis(2-i-propyl-4,7-bis-(9-anthracenyl)-indenyl)zirconium dichloride;
Dimethylsilanediylbis(2-n-butyl-4,7-bis-(9-anthracenyl)-indenyl)zirconium dichloride;
Dimethylsilanediylbis(2-s-butyl-4,7-bis-(9-anthracenyl)-indenyl)zirconium dichloride;
Dimethylsilanediylbis(2-t-butyl-4,7-bis-(9-anthracenyl)-indenyl)zirconium dichloride;
Dimethylsilanediylbis(2-n-pentyl-4,7-bis-(9-anthracenyl)-indenyl)zirconium dichloride;
Dimethylsilanediylbis(2-n-hexyl-4,7-bis-(9-anthracenyl)-indenyl)zirconium dichloride;
Dimethylsilanediylbis(2-n-heptyl-4,7-bis-(9-anthracenyl)-indenyl)zirconium dichloride;
Dimethylsilanediylbis(2-cyclopropylmethyl-4,7-bis-(9-anthracenyl)-indenyl)zirconium dichloride;
Dimethylsilanediylbis(2-cyclobutylmethyl-4,7-bis-(9-anthracenyl)-indenyl)zirconium dichloride;
Dimethylsilanediylbis(2-cyclopentylmethyl-4,7-bis-(9-anthracenyl)-indenyl)zirconium dichloride;
Dimethylsilanediylbis(2-cyclohexylmethyl-4,7-bis-(9-anthracenyl)-indenyl)zirconium dichloride;
Dimethylsilanediylbis(2-cycloheptylmethyl-4,7-bis-(9-anthracenyl)-indenyl)zirconium dichloride;
Dimethylsilanediylbis(2-(1-adamantyl)methyl-4,7-bis-(9-anthracenyl)-indenyl)zirconium dichloride;
Dimethylsilanediylbis(2-t-butyl-methyl-4,7-bis-(9-anthracenyl)-indenyl)zirconium dichloride;
Dimethylsilanediylbis(2-(1-furyl)-4,7-bis-(9-anthracenyl)-indenyl)zirconium dichloride;
Dimethylsilanediylbis(2-benzyl-4,7-bis-(9-anthracenyl)-indenyl)zirconium dichloride;
Dimethylsilanediylbis(2-phenethyl-4,7-bis-(9-anthracenyl)-indenyl)zirconium dichloride;
Dimethylsilanediylbis(2-phenylpropyl-4,7-bis-(9-anthracenyl)-indenyl)zirconium dichloride; and,
Dimethylsilanediylbis(2-phenylbutyl-4,7-bis-(9-anthracenyl)-indenyl)zirconium dichloride.

Another embodiment of this invention are the indenes of the formula 1a and the bis-indenyl-ligands of the formula 1b, as well as its double bond-isomers:

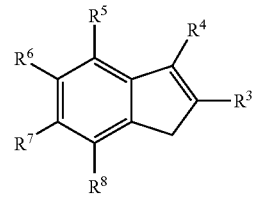

Formula 1a

-continued

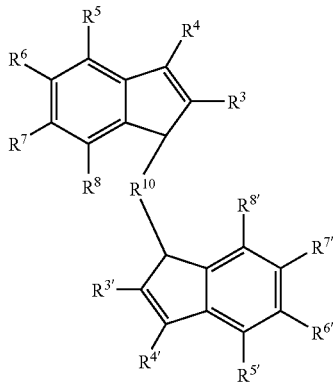

Formula 1b in which $R^3$, $R^{3'}$, $R^4$, $R^{4'}$, $R^5$, $R^{5'}$, $R^6$, $R^{6'}$, $R^7$, $R^{7'}$, $R^8$, $R^{8'}$ and $R^{10}$ have the meaning mentioned above with the proviso that $R^3$ and $R^{3'}$ each contain at least one carbon atom.

The present invention also includes a process for the racemoselective production of the transition-metal compounds of formula 1 of the invention comprising the following steps:

a) Deprotonation of the compound of formula 1a with a base, preferably n-butyl lithium.
b) If $R^{10}$ has the meaning $M^{12}R^{40}R^{41}$, where $M^{12}$, $R^{40}$, and $R^{41}$ have the meanings specified above, then the further production proceeds by the reaction of the deprotonated compounds from step (a) with $R^{40}R^{41}M^{12}X_2$ to form the compound of formula 1b, where $R^{40}$, $R^{41}$, and $M^{12}$ have the meanings specified above, and X may be the same or different and means a halogen atom, preferably chlorine, bromine, or iodine, or another leaving group, preferably triflate, tosylate, or mesylate.
c) Double deprotonation of the compound of formula 1b with a base, preferably n-butyl lithium.
d) Reacting the product from step c) $M^1Cl_4$, in which $M^1$ stands for zirconium, titanium, or hafnium, to form the compound of formula 1.

In step a), the compound of formula 1a, for example, 2-methyl-4,7-bis-(4-t-butylphenyl)indene in an inert solvent, which consists of one or more aromatic or aliphatic hydrocarbons and/or one or more polar, aprotic solvents, is deprotonated with a strong base, for example, n-butyl lithium. The deprotonation is carried out at temperatures of –70° C. to 80° C., and preferably 0° C. to 80° C. The resulting metal salt is then reacted directly, without further isolation, in step b) with a silicon compound or germanium compound that contains two leaving groups. Preferential production of the compound of formula 1b can be achieved by adjustment of the quantitative proportions. In the following step c), the bis(indenyl) silanes of formula 1b are doubly deprotonated with a strong base, such as n-butyl lithium, in an inert solvent, which consists of one or more aromatic or aliphatic hydrocarbons and/or one or more polar, aprotic solvents, and the bislithium salt formed in this way is reacted, without isolation, directly with a source of Ti, Zr, or Hf to obtain the compound of formula 1. The deprotonation is carried out at temperatures of 70° C. to 80° C., and preferably 0° C. to 80° C. Due to the nature of the ligand system of formula 1b, the metallocenes are isolated directly from the reaction mixture as pure racemic compounds.

Figure 2:
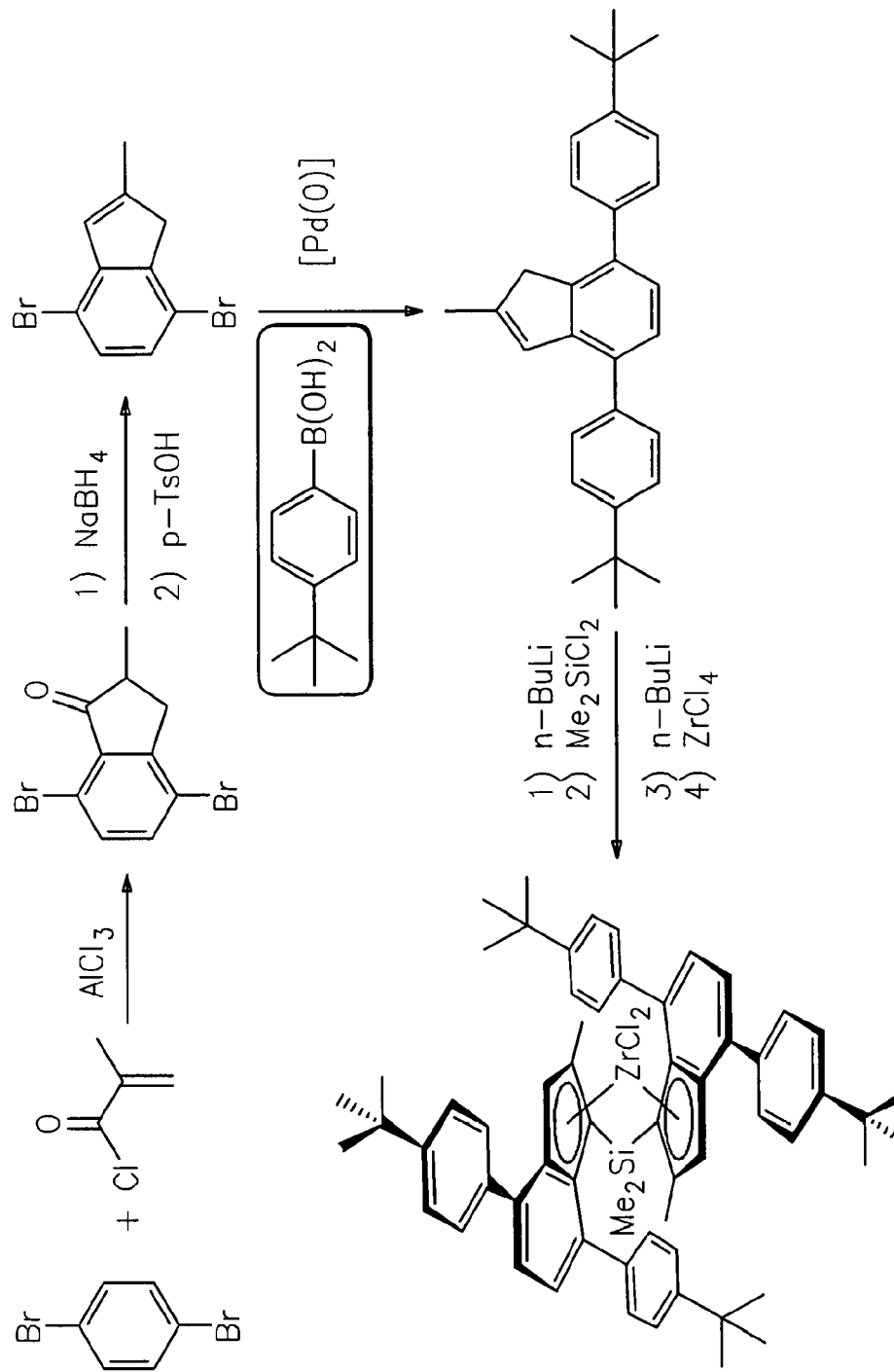
FIG. 2 is a diagrammatic illustration of individual steps of the process of the invention for producing transition-metal compounds of formula 1.

In FIG. 2, the individual steps of the process of the invention for producing transition-metal compounds of formula 1 are shown once again for the example of a preferred embodiment.

In addition, the present invention relates to a catalyst system comprising at least one compound of formula 1 and at least one cocatalyst.

A suitable cocatalyst component which may be present according to the present invention in the catalyst system comprises at least one compound of the type of an aluminoxane, a Lewis acid or an ionic compound which reacts with a metallocene to convert the latter into a cationic compound.

Aluminoxanes are oligomeric or polymeric aluminum oxy compounds, which may exist in the form of linear, cyclic, caged or polymeric structures. Although the exact structure(s) of aluminoxanes is still unknown, it is well accepted that alkylaluminoxanes have the general formula 6.

$(R-Al-O)_p$ (Formula 6).

Examples for cyclic, linear or cage structures of aluminoxanes are depicted in the formulas 7, 8 and 9:

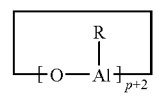

(Formula 7)

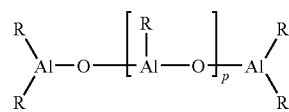

(Formula 8)

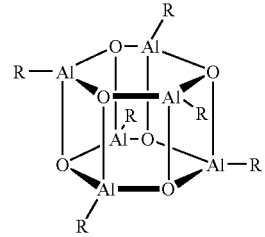

(Formula 9)

The radicals R in the formulas (6), (7), (8) and (9) can be identical or different and are each a $C_1$-$C_{20}$ group such as an alkyl group of from 1 to about 6 carbon atoms, an aryl group of from 6 to about 18 carbon atoms, benzyl or hydrogen and p is an integer from 2 to 50, preferably from 10 to 35.

Preferably, the radicals R are identical and are methyl, isobutyl, n-butyl, phenyl or benzyl, particularly preferably methyl.

If the radicals R are different, they are preferably methyl and hydrogen, methyl and isobutyl or methyl and n-butyl, with hydrogen, isobutyl or n-butyl preferably being present in a proportion of from 0.01 to 40% (number of radicals R).

The aluminoxane can be prepared in various ways by known methods. One of the methods comprises the reaction of an aluminum-hydrocarbon compound and/or a hydridoaluminum-hydrocarbon compound with water, which may be gaseous, solid, liquid or bound as water of crystallization, in an inert solvent such as toluene. To prepare an aluminoxane having different alkyl groups R, two different trialkylaluminums ($AlR_3$+$AlR'_3$) corresponding to the desired composition and reactivity are reacted with water, cf. S. Pasynkiewicz, Polyhedron 9 (1990) 429 and EP-A-0 302 424.

Regardless of the method of preparation, all aluminoxane solutions have in common a variable content of unreacted aluminum starting compound which is present in free form or as an adduct.

Furthermore, instead of the aluminoxane compounds of the formulas 6, 7, 8 or 9, it is also possible to use modified aluminoxanes in which the hydrocarbon radicals or hydrogen atoms have been partly replaced by alkoxy, aryloxy, siloxy or amide radicals.

The amounts of aluminoxane and metallocene used in the preparation of the supported catalyst system can be varied within a wide range. However, it has been found to be advantageous to use the metallocene compound of formula 1 and the aluminoxane compounds in such amounts that the atomic ratio of aluminum from the aluminoxane compounds to the transition metal from the metallocene compound is in the range from 10:1 to 1000:1, preferably from 20:1 to 500:1 and in particular in the range from 30:1 to 400:1. In the case of methylaluminoxane, preference is given to using 30 wt.-% strength toluene solutions, but the use of 10 wt.-% strength solutions is also possible.

As Lewis acid, preference is given to using compounds of the formula 10

$$M^2 X^1 X^2 X^3 \quad \text{(Formula 10)}$$

where $M^2$ is an element of Group 13 of the Periodic Table of Elements, in particular B, Al or Ga, preferably B or Al, and $X^1$, $X^2$ and $X^3$ are the same or different and each are a hydrogen atom, an alkyl group of from 1 to about 20 carbon atoms, an aryl group of from 6 to about 15 carbon atoms, alkylaryl, arylalkyl, haloalkyl or haloaryl each having from 1 to 10 carbon atoms in the alkyl radical and from 6-20 carbon atoms in the aryl radical or fluorine, chlorine, bromine or iodine. Preferred examples for $X^1$, $X^2$ and $X^3$ are methyl, propyl, isopropyl, isobutyl or trifluoromethyl, unsaturated groups such as aryl or haloaryl like phenyl, tolyl, benzyl groups, p-fluorophenyl, 3,5-difluorophenyl, pentachlorophenyl, pentafluorophenyl, 3,4,5-trifluorophenyl and 3,5-di(trifluoromethyl)phenyl.

Preferred Lewis acids are trimethylaluminum, triethylaluminum, triisobutylaluminum, tributylaluminum, trifluoroborane, triphenylborane, tris(4-fluorophenyl)borane, tris(3,5-difluorophenyl)borane, tris(4-fluoromethylphenyl)borane, tris(2,4,6-trifluorophenyl)borane, tris(penta-fluorophenyl) borane, tris(tolyl)borane, tris(3,5-dimethyl-phenyl)borane, tris(3,5-difluorophenyl)borane and/or tris(3,4,5-trifluorophenyl)borane.

Particular preference is given to tris(pentafluorophenyl) borane.

As ionic cocatalysts, preference is given to using compounds which contain a non-coordinating anion such as tetrakis(pentafluorophenyl)borate, tetraphenylborate, $SbF_6^-$, $CF_3SO_3^-$ or $ClO_4^-$. Suitable counterions are either Lewis acid or Broenstedt acid cation.

As Broensted acids, particular preference is given to protonated amine or aniline derivatives such as methylammonium, anilinium, dimethylammonium, diethylammonium, N-methylanilinium, diphenylammonium, N,N-dimethylanilinium, trimethylammonium, triethylammonium, tri-n-butylammonium, methyldiphenylammonium, pyridinium, p-bromo-N,N-dimethylanilinium or p-nitro-N,N-dimethylanilinium, Suitable Lewis-acid cations are cations of the formula 11

$$[(Y^{a+})Q_1 Q_2 \ldots Q_z]^{d+} \quad \text{(Formula 11)}$$

where Y is an element of Groups 1 to 16 of the Periodic Table of the Elements, $Q_1$ to $Q_z$ are singly negatively charged groups such as $C_1$-$C_{28}$-alkyl, $C_6$-$C_{15}$-aryl, alkylaryl, arylalkyl, haloalkyl, haloaryl each having from 6 to 20 carbon atoms in the aryl radical and from 1 to 28 carbon atoms in the alkyl radical, cycloalkyl groups of from 3 to about 10 carbon atoms, which may in turn bear alkyl groups of from 1 to about 10 carbon atoms as substitutents, halogen, alkoxy groups of from 1 to 28 carbon atoms, aryloxy groups of from 6 to 15 carbon atoms, silyl or mercaptyl groups.

a is an integer from 1-6, z is an integer from 0 to 5 and d corresponds to the difference a-z, but d is larger than or equal to 1

Particularly suitable cations are carbonium cations such as triphenylcarbenium, oxonium cations, sulfonium cations such as tetrahydrothiophenium, phosphonium cations such as triethylphosphonium, triphenylphosphonium and diphenylphosphonium, and also cationic transition metal complexes such as the silver cation and the 1,1'-dimethylferrocenium cation.

Preferred ionic compounds which can be used according to the present invention include:

triethylammoniumtetra(phenyl)borate,
tributylammoniumtetra(phenyl)borate,
trimethylammoniumtetra(tolyl)borate,
tributylammoniumtetra(tolyl)borate,
tributylammoniumtetra(pentafluorophenyl)borate,
tributylammoniumtetra(pentafluorophenyl) aluminate,
tripropylammoniumtetra(dimethylphenyl)borate,
tributylammoniumtetra(trifluoromethylphenyl) borate,
tributylammoniumtetra(4-fluorophenyl)borate,
N,N-dimethylcyclohexylammoniumtetrakis(pentafluorophenyl)borate,
N,N-dimethylbenzylammoniumtetrakis(pentafluorophenyl) borate
N,N-dimethylaniliniumtetra(phenyl)borate,
N,N-diethylaniliniumtetra(phenyl)borate,
N,N-dimethylaniliniumtetrakis(pentafluorophenyl)borate,
N,N-dimethylaniliniumtetrakis(pentafluorophenyl)aluminate,
di(propyl)ammoniumtetrakis(pentafluorophenyl)borate,
di(cyclohexyl)ammoniumtetrakis(pentafluorophenyl)borate,
triphenylphosphoniumtetrakis(phenyl)borate,
triethylphosphoniumtetrakis(phenyl)borate,
diphenylphosphoniumtetrakis(phenyl)borate,
tri(methylphenyl)phosphoniumtetrakis(phenyl)borate,
tri(dimethylphenyl)phosphoniumtetrakis(phenyl)borate,
triphenylcarbeniumtetrakis(pentafluorophenyl)borate,
triphenylcarbeniumtetrakis(pentafluorophenyl)aluminate,
triphenylcarbeniumtetrakis(phenyl)aluminate,
ferroceniumtetrakis(pentafluorophenyl)borate and/or
ferroceniumtetrakis(pentafluorophenyl)aluminate, Preference is given to triphenylcarbeniumtetrakis(pentafluorophenyl)borate, N,N-dimethylcyclohexylammoniumtetrakis(pentafluorophenyl)borate or N,N-dimethylbenzylammoniumtetrakis(pentafluorophenyl)borate.

It is also possible to use mixtures of all of the above and below mentioned cation-forming compounds. Preferred mixtures comprise aluminoxanes and an ionic compound, and/or a Lewis acid.

Other useful cocatalyst components are likewise borane or carborane compounds such as 7,8-dicarbaundecaborane(13),
undecahydrido-7,8-dimethyl-7,8-dicarbaundecaborane,
dodecahydrido-1-phenyl-1,3-dicarbanonaborane,
tri(butyl)ammoniumun decahydrido-8-ethyl-7,9-dicarbaundecaborate,
4-carbanonaborane(14),
bis(tri(butyl)ammonium)nonaborate,
bis(tri(butyl)ammonium)undecaborate,
bis(tri(butyl)ammonium)dodecaborate,
bis(tri(butyl)ammonium)decachlorodecaborate,
tri(butyl)ammonium-1-carbadecaborate, tri(butyl)ammonium-1-carbadodecaborate,
tri(butyl)ammonium-1-trimethylsilyl-1-carbadecaborate,
tri(butyl)ammoniumbis(nonahydrido-1,3-dicarbanonaborato)cobaltate(III), tri(butyl)ammonium
bis(undecahydrido-7,8-dicarbaundecaborato)ferrate(III).

The amount of Lewis acids or ionic compounds having Lewis-acid or Broensted-acid cations is preferably from 0.1 to 20 equivalents, preferably from 1 to 10 equivalents, based on the metallocene compound of the formula 1.

Combinations of at least one Lewis base with bimetallic compounds of the type $R_i^{17}M^3(-O-M^3R_j^{18})_v$ or $R_i^{18}M^3(-O-M^3R_j^{17})_v$ (formula 12), as described in Patent Application WO 99/40,129, are likewise important as cocatalyst systems.

In this regard, $R^{17}$ and $R^{18}$ are the same or different and represent a hydrogen atom, a halogen atom, a $C_1$-$C_{40}$ carbon-containing group, especially an alkyl group of from 1 to about 20 carbon atoms, haloalkyl of from 1 to about 20 carbon atoms, alkoxy of from 1 to about 10 carbon atoms, aryl of from 6 to about 20 carbon atoms, haloaryl of from 6 to about 20 carbon atoms, aryloxy of from 6 to about 20 carbon atoms, arylalkyl of from 7 to about 40 carbon atoms, haloarylalkyl of from 7 to about 40 carbon atoms, alkylaryl of from 7 to about 40 carbon atoms, or haloalkylaryl of from 7 to about 40 carbon atoms. $R^{17}$ may also be an —$OSiR^{51}_3$ group, in which the $R^{51}$ groups are the same or different and have the same meaning as $R^{17}$, $M^3$ is the same or different and represents an element of main group III of the periodic table of elements, i, j, and v each stands for a whole number 0, 1, or 2, and i+j+v is not equal to 0.

Preferred cocatalyst systems are the compounds of formulas (A) and (B)

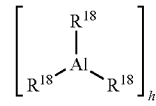

where $R^{17}$ and $R^{18}$ have the same meaning as specified above.

Furthermore, compounds that are generally to be regarded as preferred are those formed by the reaction of at least one compound of formulas (C) and/or (D) and/or (E) with at least one compound of formula (F).

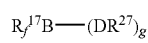  (C)

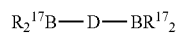  (D)

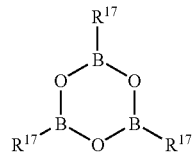  (E)

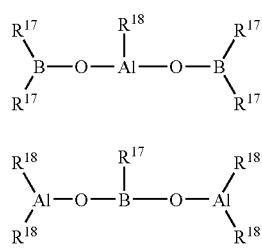  (F)

in which $R^{27}$ may be a hydrogen atom or a boron-free $C_1$-$C_{40}$ carbon-containing group, such as an alkyl of from 1 to about 20 carbon atoms, aryl of from 6 to about 20 carbon atoms, arylalkyl of from 7 to about 40 carbon atoms, and alkylaryl of from 7 to about 40 carbon atoms, and in which $R^{17}$, $R^{18}$ have the same meaning as specified above, D is an element of main Group VI of the periodic table of elements or an $NR^{61}$ group, where $R^{61}$ is a hydrogen atom or a $C_1$-$C_{20}$ hydrocarbon group, such as alkyl of from 1 to about 20 carbon atoms or aryl of from 6 to about 20 carbon atoms, f is a whole number from 0 to 3, g is a whole number from 0 to 3 where f+g corresponds to the valency of Boron, and h is a whole number from 1 to 10.

The bimetallic compounds of formula 12 are possibly combined with an organometallic compound of formula 13, i.e., $[M^4R^{19}_q]_k$, in which $M^4$ is an element of main Group I, II, or III of the periodic table of the elements, $R^{19}$ is the same or different and represents a hydrogen atom, a halogen atom, a $C_1$-$C_{40}$ carbon-containing group, an alkyl group of from 1 to about 20 carbon atoms, an aryl group of from about 6 to about 40 carbon atoms, arylalkyl of from 7 to about 40 carbon atoms, and alkylaryl of from 7 to about 40 carbon atoms, q is a whole number from 1 to 3, and k is a whole number from 1 to 4.

The organometallic compounds of formula 13 are preferably neutral Lewis acids, in which $M^4$ stands for lithium, magnesium, and/or aluminum, especially aluminum. Examples of preferred organometallic compounds of formula 13 are trimethylaluminum, triethylaluminum, triisopropylaluminum, trihexylaluminum, trioctylaluminum, tri-n-butylaluminum, tri-n-propylaluminum, triisoprene aluminum, dimethyl aluminum monochloride, aluminum monochloride, diisobutyl aluminum monochloride, methyl aluminum sesquichloride, ethyl aluminum sesquichloride, dimethyl aluminum hydride, aluminum hydride, diisopropyl aluminum hydride, dimethyl aluminum(trimethylsiloxide), dimethyl aluminum(triethylsiloxide), phenylalan, pentafluorophenylalan, and o-tolylalan.

The catalyst system of the invention contains an organoboroaluminum compound, which contains units of formula 12, as the cocatalytically active chemical compound. Compounds of formula 12 in which $M^3$ stands for boron or aluminum are preferred. The compounds that contain units of formula 12 may be present as monomers or as linear, cyclic, or cage-like oligomers. Two or more chemical compounds that contain units of formula 12 may also form dimers, trimers, or higher combinations among themselves by Lewis acid-base interactions.

Preferred cocatalytically active bimetallic compounds correspond to formulas 14 and 15,

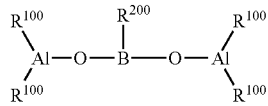 (formula 14)

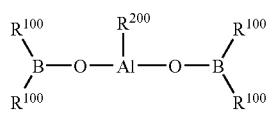 (formula 15)

in which $R^{100}$ and $R^{200}$ are the same or different and have the same meaning as the substituents $R^{17}$ or $R^{18}$ in formula 12.

Examples of the cocatalytically active compounds of formulas 14 and 15 are

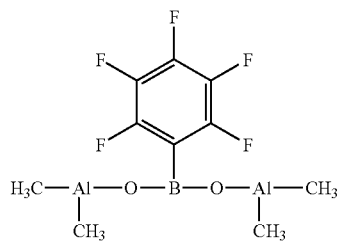

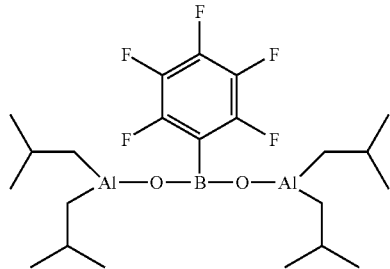

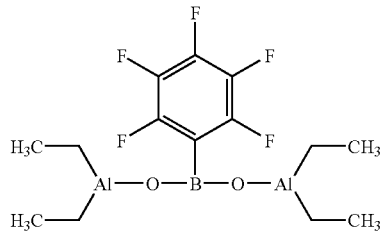

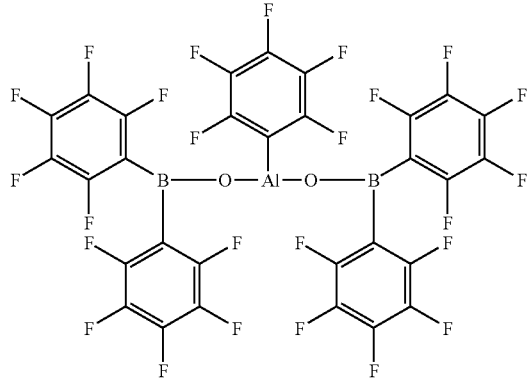

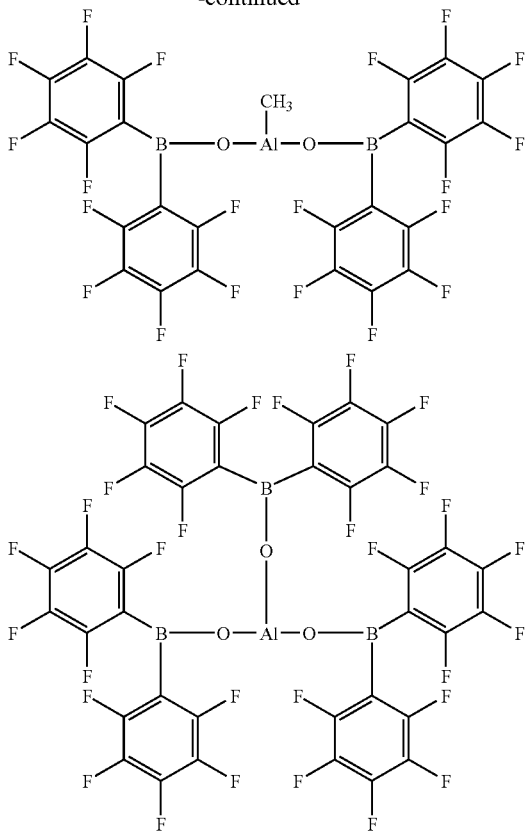

The compounds named in EP-A-924,223, DE 196 22 207.9, EP-A-601,830, EP-A-824,112, EP-A-824,113, WO 99/06,414, EP-A-811,627, WO 97/11,775, DE 196 06 167.9 and DE 198 04 970 can be used as additional cocatalysts, which may be present in unsupported or supported form.

The amount of cocatalysts of formula 12 and/or 14 and/or 15 used in the catalyst of the present invention can vary from 0.1 to 500 equivalents, preferably from 1 to 300 equivalents, most preferably from 5 to 150 equivalents, based on the used amount of metallocene compound of the formula 1.

The catalyst system of the present invention can further comprise, as additional component, a metal compound of the formula 16, $$M^5(R^{22})_r(R^{23})_s(R^{24})_t$$ (Formula 16)

wherein
$M^5$ is an alkali, an alkali earth metal or a metal of Group 13 of the Periodic Table of the Elements,
$R^{22}$ is a hydrogen atom, alkyl of from 1 to about 10 carbon atoms, aryl of from 6 to about 15 carbon atoms, or alkylaryl or arylalkyl each having from 1 to 10 carbon atoms in the alkyl part and from 6 to 20 carbon atoms in the aryl part,
$R^{23}$ and $R^{24}$ are each a hydrogen atom, a halogen atom, alkyl of from 1 to about 10 carbon atoms, $C_6$-$C_{15}$-aryl of from about 6 to about 15 carbon atoms, or alkylaryl, arylalkyl or alkoxy each having from 1 to 10 carbon atoms in the alkyl part and from 6 to 20 carbon atoms in the aryl radical,
r is an integer from 1 to 3 and s and t are integers from 0 to 2, where the sum r+s+t corresponds to the valency of $M^5$,
where this component is not identical with the above mentioned cocatalyst compounds. It is also possible to use mixtures of various metal compounds of the formula 16.

Among the metal compounds of the formula 16 preference is given to those in which $M^5$ is lithium, magnesium or aluminum and $R^{23}$ and $R^{24}$ are each alkyl of from 1 to about 10 carbon atoms. Particularly preferred metal compounds of the formula 16 are n-butyllithium, n-butyl-n-octyl-magnesium, n-butyl-n-heptylmagnesium, tri-n-hexylaluminum, triisobutylaluminum, triethylaluminum, trimethylaluminum or mixtures thereof.

If a metal compound of the formula 16 is used, it is preferably present in the catalyst system in such an amount that the molar ratio of $M^5$ to the transition metal from the metallocene compound of formula 1 is from 800:1 to 1:1, in particular from 200:1 to 2:1.

The support component of the catalyst system of the present invention can be any organic or inorganic inert solid or a mixture of such solids, in particulate porous solids such as hydrotalcites, talc, inorganic oxides and finely divided polymer powders.

Suitable inorganic oxides, which are preferably employed include from the Periodic Table of Elements Groups 1, 2, 3, 4, 5, 12, 13 and 14 metal oxides such as silicon dioxide, aluminum oxide, aluminosilicates, zeolites, MgO, $ZrO_2$, $TiO_2$ or $B_2O_3$, CaO, ZnO, $ThO_2$, $Na_2O$, $K_2O$, $LiO_2$ or mixed oxides like Al/Si oxides, Mg/Al oxides or Al/Mg/Si oxides. Other suitable inorganic support materials are $Na_2CO_3$, $K_2CO_3$, $CaCO_3$, $MgCl_2$, $Na_2SO_4$, $Al_2(SO_4)_3$, $BaSO_4$, $KNO_3$, $Mg(NO_3)_2$ and $Al(NO_3)_3$.

Suitable polymer powders are homopolymers, copolymers, crosslinked polymers or polymer blends. Examples of such polymers are polyethylene, polypropylene, polybutene, polystyrene, divinylbenzene-crosslinked polystyrene, polyvinyl chloride, acrylonitrile-butadiene-styrene copolymer, polyamide, polymethacrylate, polycarbonate, polyester, polyacetal or polyvinyl alcohol.

The preferred support materials have a specific surface area in the range from 10 to 1000 $m^2/g$, a pore volume in the range from 0.1 to 5 $cm^3/g$ and a mean particle size of from 1 to 500 μm. Preference is given to supports having a specific surface area in the range from 50 to 500 $m^2/g$, a pore volume in the range from 0.5 to 3.5 $cm^3/g$ and a mean particle size in the range from 5 to 250 μm. Particular preference is given to supports having a specific surface area in the range from 200 to 400 $m^2/g$, a pore volume in the range from 0.8 to 3.0 $cm^3/g$ and a mean particle size of from 10 to 100 μm.

The support materials can be thermally and/or chemically be pretreated in order to adjust certain properties of the carrier such as the water and/or the hydroxyl group content.

If the support material has a low moisture content or residual solvent content, dehydration or drying before use can be omitted. If this is not the case, as when using silica gel as support material, dehydration or drying is advisable. Thermal dehydration or drying of the support material can be carried out under reduced pressure with or without simultaneous inert gas blanketing (nitrogen). The drying temperature is in the range from 80° C. to 1000° C., preferably from 150° C. to 800° C. and most preferred from 150° C. to 400° C. The duration of the drying process can be from 1 to 24 hours. But shorter or longer drying periods are also possible.

In a preferred embodiment of the present invention, support materials with a weight loss on dryness (LOD) of 0.5 wt. % or less, and even more preferred with a LOD of 0.3 wt % or less are used. Higher amounts of physically adsorbed water up to 1 wt % are possible, but result in reduced catalyst activities. The loss on ignition (LOI) of the support material is preferably 1 wt % or greater or even more preferred between 1.5 and 3.5 wt %. The weight loss on dryness (LOD) is thereby defined as the weight loss between room temperature and 300° C. and the weight loss on ignition (LOI) as the weight loss between 300° C. and 1000° C.

In addition or alternatively, dehydration or drying of the support material can also be carried out by chemical means, by reacting the adsorbed water and/or the surface hydroxyl groups with suitable passivating agents. Reaction with the passivating reagent can convert the hydroxyl groups completely or partially into a form, which does not show any adverse interaction with the catalytically active centers. Suitable passivating agents are silicon halides, silanes or amines, eg. silicon tetrachloride, chlorotrimethylsilane, dichlorodialkylsilanes, dimethylaminotrichlorosilane, N,N-dimethylanilin or N,N-dimethylbenzylamine or organometallic compounds of aluminum, boron and magnesium, eg. aluminoxanes, trimethylaluminum, triethylaluminum, triisobutylaluminum, diisobutylaluminum hydride, triethylborane or dibutylmagnesium.

As outlined above, organic support materials such as finely divided polymer powders, can also be used and should, before use, likewise be freed from any adhering moisture, solvent residues or other impurities by means of appropriate purification and drying operations.

Preference is given to using silica gels having the defined parameters as support materials. Spray dried silica grades, which inherently exhibit meso and macro pores, cavities and channels are preferred over granular silica grades.

The supported catalyst system according to this invention can be made in various ways.

In one embodiment of the present invention, at least one of the above-described metallocene components of formula 1 is brought into contact in a suitable solvent with at least one cocatalyst component, preferably giving a soluble reaction product, an adduct or a mixture. The obtained composition is mixed with the dehydrated or passivated support material, the solvent is removed and the resulting supported metallocene catalyst system is dried to ensure that the solvent is completely or mostly removed from the pores of the support material. The supported catalyst is obtained as a free-flowing powder.

As an example, the process for preparing a free-flowing and, if desired, prepolymerized supported catalyst system comprises the following steps:

a) preparing a metallocene/cocatalyst mixture in a suitable solvent or suspension medium, where the metallocene component has one of the above-described structures, b) applying the metallocene/cocatalyst mixture to a porous, preferably inorganic, if necessary thermally or chemically pretreated support, c) removing the major part of solvent from the resulting mixture, d) isolating the supported catalyst system and e) if desired, prepolymerizing the resulting supported catalyst system with one or more olefinic monomer(s), to obtain a prepolymerized supported catalyst system.

In another embodiment of this invention the metallocene/cocatalyst composition is mixed with the dehydrated or passivated support material, the supported catalyst is recovered and optionally washed with an aromatic hydrocarbon and/or paraffinic hydrocarbon solvent. The isolated catalyst is then dispersed in a non-reactive suspension media such as a paraffinic hydrocarbon solvent, a mineral oil or a wax or mixtures thereof.

In a further embodiment of this invention the catalyst can be prepared according to the procedure disclosed in WO 06/60544, WO 00/05277 and WO 98/01481.

As an example, in WO 06/60544, a free flowing and, if desired, prepolymerized supported catalyst system is prepared comprising the following steps:

a) contacting at least one support material with a first portion of at least one co-catalyst in a suitable solvent b) impregnating the co-catalyst loaded support with a suspension or solution, which comprises at least one metallocene and a second portion of at least one co-catalyst in a suitable solvent c) isolating the supported catalyst system and f) if desired, prepolymerizing the resulting supported catalyst system with one or more olefinic monomer(s), to obtain a prepolymerized supported catalyst system.

Thus, as an example, the process according to WO 06/60544 for preparing a free-flowing and, if desired, prepolymerized supported catalyst system comprises the following steps:

a) Contacting a support material with a first composition which includes at least one aluminoxane in a first solvent at a temperature of about 10 to 30° C. followed by keeping the mixture at about 20° C. for 0 to 12 hours, subsequently heating the resulting mixture to a temperature of 30 to 200° C. and keeping the mixture at 30 to 200° C. for 30 minutes to 20 hours, optionally followed by removing all or part of the first solvent and/or optionally followed by one or more washing step(s) using a suitable solvent, b) Suspending and/or dissolving, respectively, at least one metallocene of formula 1 and a second portion of an aluminoxane or of a mixture of aluminoxanes or of an ionic compound and/or a Lewis acid in a second solvent or suspension medium at a temperature of 0 to 100° C., optionally followed by a preactivation time of 1 minute to 200 hours at a temperature of 10 to 100°, c) Applying the mixture prepared in b) to the aluminoxane loaded support material produced in a), at a temperature of 10 to 100° C. and a contact time of 1 minute to 24 hours, d) Removing the major part of the solvent from the resulting mixture and optionally washing the resulting supported catalyst with a suitable solvent, e) Isolating the supported catalyst system and f) Optionally prepolymerizing the resulting supported catalyst system with one or more olefinic monomer(s), to obtain a prepolymerized supported catalyst system.

More specifically, as an example, the process according to WO 06/60544 for preparing a free-flowing and, if desired, prepolymerized supported catalyst system comprises the following steps:

a) Contacting a support material with a first composition which includes at least 5 mmol of an aluminoxane or of a mixture of aluminoxanes per g support material in a first solvent at a temperature of about 20° C. followed by keeping the mixture at about 20° C. for 0.15 to 2 hours, subsequently heating the resulting mixture to a temperature of 50 to 160° C. and keeping the mixture at 50 to 160° C. for 1 to 6 hours, optionally followed by removing all or part of the first solvent and/or optionally followed by one or more washing step(s) using a suitable solvent, b) Suspending and/or dissolving, respectively, at least 0.5 mmole of a second portion of an aluminoxane or of a mixture of aluminoxanes per g support material and at least 0.1 mol % of the employed second portion of an aluminoxane or of a mixture of aluminoxanes per g support material of at least one metallocene of formula 1 in a second solvent or suspension medium at a temperature of 20 to 50° C., optionally followed by a preactivation time of 1 minute to 200 hours at a temperature of 20 to 30°, c) Applying the mixture prepared in b) to the aluminoxane loaded support material produced in a), at a temperature of 10 to 100° C. and a contact time of 1 minute to 24 hours, d) Removing the major part of the solvent from the resulting mixture and e) Optionally washing the resulting supported catalyst with a suitable solvent, and/or drying the resulting supported catalyst at temperatures of 30 to 60° C., and f) Optionally prepolymerizing the resulting supported catalyst system with one or more olefinic monomer(s), to obtain a prepolymerized supported catalyst system.

In a preferred embodiment, as an example, the process according to WO 06/60544 for preparing a free-flowing and, if desired, prepolymerized supported catalyst system comprises the following steps:

a) Contacting an optionally thermally pretreated silica support material with at least 10 mmol of an aluminoxane per g support material in toluene at a temperature of about 20° C. followed by subsequently heating the resulting mixture to a temperature of 50 to 110° C. and keeping the mixture at 50 to 110° C. for 1 to 6 hours, optionally followed by removing all or part of the toluene, and/or optionally followed by one or more washing step(s) using a suitable solvent, b) Suspending and/or dissolving, respectively, at least 0.5 mmole of a second portion of an aluminoxane per g support material and at least 0.1 mol % of the employed second portion of an aluminoxane or of a mixture of aluminoxanes per g support material of at least one metallocene of formula 1 in toluene at a temperature of 20 to 50° C., optionally followed by a preactivation time of 1 minute to 200 hours at a temperature of 20 to 30°, c) Applying the mixture prepared in b) to the aluminoxane loaded support material produced in a), at a temperature of 10 to 100° C. and a contact time of 1 minute to 24 hours, d) Removing the major part of the toluene from the resulting mixture and e) Optionally washing the resulting supported catalyst with a suitable solvent, and/or drying the resulting supported catalyst at temperatures of 30 to 60° C., and f) Optionally prepolymerizing the resulting supported catalyst system with one or more olefinic monomer(s), to obtain a prepolymerized supported catalyst system.

In a more preferred embodiment, as an example, the process according to WO 06/60544 for preparing a free-flowing and, if desired, prepolymerized supported catalyst system comprises the following steps:

a) Contacting an optionally thermally pretreated silica support material with a weight loss on dryness (LOD) of 0.5 wt. % or less and a weight loss on ignition (LOI) of 1.0 wt. % or greater with a first composition which includes at least 10 mmol of methylaluminoxane per g support material in toluene at a temperature of about 20° C. followed by subsequently heating the resulting mixture to a temperature of 110° C. and keeping the mixture at 110° C. for 1 to 6 hours, optionally followed by removing all or part of the toluene, and/or optionally followed by one or more washing step(s) using a suitable solvent, b) Suspending and/or dissolving, respectively, at least 1 mmole of a second portion of methylaluminoxane per g support material and at least 0.1 mol % of the employed second portion of methylaluminoxane per g support material of at least one metallocene of formula 1 in toluene at a temperature of 20 to 50° C., optionally followed by a preactivation time of 1 minute to 200 hours at a temperature of 20 to 30°, c) Applying the mixture prepared in b) to the methylaluminoxane loaded support material produced in a), by passing the impregnation suspension or solution b) through the methylaluminoxane loaded support material in a direct flow or by using an incipient wetness impregnation technique, where the volume of the impregnation suspension or solution or the total liquid volume used in the impregnation step, respectively, does not exceed 250% of the total pore volume of the support material, at a temperature of 10 to 100° C. and a contact time of 1 minute to 24 hours, d) Removing the major part of the toluene from the resulting mixture and e) Optionally washing the resulting supported catalyst with a suitable solvent, and/or drying the resulting supported catalyst at temperatures of 30 to 60° C., and f) Optionally prepolymerizing the resulting supported catalyst system with one or more olefinic monomer(s), to obtain a prepolymerized supported catalyst system.

In a particular preferred embodiment, as an example, the process according to WO 06/60544 for preparing a free-flowing and, if desired, prepolymerized supported catalyst system comprises the following steps:

a) Contacting an optionally thermally pretreated silica support material with a weight loss on dryness (LOD) of 0.3 wt. % or less and a weight loss on ignition (LOT) between 1.5 and 3.5 wt. %, with at least 10 mmol of methylaluminoxane per g support material in toluene at a temperature of about 20° C. followed by subsequently heating the resulting mixture to a temperature of 110° C. and keeping the mixture at 110° C. for 1 to 6 hours, optionally followed by removing all or part of the toluene, and/or optionally followed by one or more washing step(s) using a suitable solvent, b) Suspending and/or dissolving, respectively, at least 1 mmole of a second portion of methylaluminoxane per g support material and at least 0.1 mol % of the employed second portion of methylaluminoxane per g support material of at least one metallocene of formula 1 in toluene at a temperature of 20 to 50° C., optionally followed by a preactivation time of 1 minute to 200 hours at a temperature of 20 to 30°, c) Applying the mixture prepared in b) to the methylaluminoxane loaded support material produced in a), by passing the impregnation suspension or solution b) through the aluminoxane loaded support material a) in a direct flow or by using an incipient wetness impregnation technique, where the volume of the impregnation suspension or solution or the total liquid volume used in the impregnation step, respectively, does not exceed 250% of the total pore volume of the support material, at a temperature of 10 to 100° C. and a contact time of 1 minute to 24 hours, d) Removing the major part of the toluene from the resulting mixture and e) Optionally washing the resulting supported catalyst with a suitable solvent, and/or drying the resulting supported catalyst at temperatures of 30 to 60° C., and f) Optionally prepolymerizing the resulting supported catalyst system with one or more olefinic monomer(s), to obtain a prepolymerized supported catalyst system.

According to the present invention, for preparing a free-flowing and, if desired, prepolymerized supported catalyst system, in step b) of the catalyst preparations as mentioned above, instead of an aluminoxane or a mixture of aluminoxanes, at least one alkyl compound of elements of main Groups I to III of the Periodic Table, for example a magnesium alkyl, a lithium alkyl or an aluminum alkyl like trimethylaluminum, triethylaluminum, triisobutyllaluminum, triisopropylaluminum, trihexylaluminum, trioctylaluminum, tri-n-butylaluminum, tri-n-propylaluminum, triisoprene aluminum, dimethyl aluminum monochloride, aluminum monochloride, diisobutyl aluminum monochloride, methyl aluminum sesquichloride, ethyl aluminum sesquichloride, dimethyl aluminum hydride, aluminum hydride, diisopropyl aluminum hydride, dimethyl aluminum(trimethylsiloxide), dimethyl aluminum (triethylsiloxide), phenylalan, pentafluorophenylalan, and o-tolylalan, can be used. Preferred aluminum alkyls are trimethylaluminum, triethylaluminum, triisobutyllaluminum.

In an even further embodiment of the present invention a free flowing and, if desired, prepolymerized supported catalyst system is prepared comprising the following steps:

a) preparing a trialkylaluminium/borinic acid mixture in a suitable solvent or suspension medium b) applying the trialkylaluminium/borinic acid mixture to a porous, preferably inorganic, if necessary thermally or chemically pretreated support, which was prior treated with a base like N,N-diethylbenzylamine, N,N-dimethylbenzylamine, N-benzyldimethylamine, N-benzyldiethylamine, N-benzylbutylamine, N-benzyl tertbutylamine, N-benzylisopropylamine, N-benzylmethylamine, N-benzylethylamine, N-benzyl-1-phenylethylamine, N-benzyl-2-phenylethylamine, N,N-dimethylbenzylamine, N,N-diethylbenzylamine, N-methyl-N-ethylbenzylamine, N-methyldibenzylamine and N-ethyldi(benzyl)amine, c) removing the major part of solvent from the resulting mixture to obtain a supported cocatalyst, d) preparing a metallocene/supported cocatalyst mixture in a suitable solvent or suspension medium, where the metallocene of formula 1 is optionally treated with additional trialkylaluminum, e) isolating the supported catalyst system and f) if desired, prepolymerizing the resulting supported catalyst system with one or more olefinic monomer(s), to obtain a prepolymerized supported catalyst system.

Preferred solvents for the preparation of the metallocene/cocatalyst mixture are hydrocarbons and hydrocarbon mixtures, which are liquid at the selected reaction temperature and in which the individual components preferably dissolve. The solubility of the individual components is, however, not a prerequisite as long as it is ensured that the reaction product of metallocene and cocatalyst components is soluble in the solvent selected. Suitable solvents are alkanes such as pentane, isopentane, hexane, isohexane, heptane, octane and nonane, cycloalkanes such as cyclopentane and cyclohexane and aromatics such as benzene, toluene, ethylbenzene and diethylbenzene. Very particular preference is given to toluene, heptane and ethylbenzene.

For a preactivation, the metallocene in the form of a solid is dissolved in a solution of the cocatalyst in a suitable solvent. It is also possible to dissolve the metallocene separately in a suitable solvent and subsequently to combine this solution with the cocatalyst solution. Preference is given to using toluene. The preactivation time is from 1 minute to 200 hours. The preactivation can take place at room temperature of 25° C. In individual cases, the use of higher temperatures can reduce the required preactivation time and give an additional increase in activity. Elevated temperatures in this case refer to a range from 25° C. to 100° C.

The preactivated solution or the metallocene/cocatalyst mixture is subsequently combined with an inert support material, usually silica gel, which is in the form of a dry powder or as a suspension in one of the above mentioned solvents. The support material is preferably used as powder. The preactivated metallocene/cocatalyst solution or the metallocene/cocatalyst mixture can be either added to the initially charged support material, or else the support material can be introduced into the initially charged solution.

The volume of the preactivated solution or the metallocene/cocatalyst mixture can exceed 100% of the total pore volume of the support material used or else be up to 100% of the total pore volume.

The temperature at which the preactivated solution or the metallocene/cocatalyst mixture is brought into contact with the support material can vary within the range from 0° C. to 100° C. However, lower or higher temperatures are also possible.

While the solvent is completely or mostly removed from the supported catalyst system, the mixture can be stirred and, if desired, also heated. Preferably, both the visible portion of the solvent and the portion in the pores of the support material are removed. The removal of the solvent can be carried out in a conventional way using reduced pressure and/or purging with inert gas. During the drying process, the mixture can be heated until the free solvent has been removed, which usually takes from 1 to 3 hours at a preferred temperature of from 30° C. to 60° C. The free solvent is the visible portion of the solvent in the mixture. For the purposes of the present invention, residual solvent is the portion present in the pores.

As an alternative to the complete removal of the solvent, the supported catalyst system can also be dried until only a certain residual solvent content is left, with the free solvent having been completely removed. Subsequently, the supported catalyst system can be washed with a low-boiling point hydrocarbon such as pentane or hexane and dried again.

The supported catalyst system prepared according to the present invention can be used either directly for the polymerization of olefins or be prepolymerized with one or more olefinic monomers, with or without the use of hydrogen as molar mass regulating agent, prior to use in a polymerization process. The procedure for the prepolymerization of supported catalyst systems is described in WO 94/28034.

It is possible to add, during or after the preparation of the supported catalyst system, a small amount of an olefin, preferably an alpha-olefin such as styrene or phenyldimethylvinylsilane as activity-increasing component or an antistatic, as described in U.S. Ser. No. 08/365,280. The molar ratio of additive to metallocene component of formula 1 is preferably from 1:1000 to 1000:1, very particularly preferably from 1:20 to 20:1.

The present invention also provides a process for preparing a polyolefin by polymerization of one or more olefins in the presence of the catalyst system of the present invention comprising at least one transition metal component of the formula 1. For the purposes of the present invention, the term polymerization refers to both homopolymerization and copolymerization and the term copolymerization includes terpolymerisation or copolymerisation of more than three different monomers.

Preference is given to polymerizing olefins of the formula $R'''$—CH=CH—$R''$, where $R'''$ and $R''$ are identical or different and are each a hydrogen atom or a radical having from 1 to 20 carbon atoms, in particular from 1 to 10 carbon atoms, and $R'''$ and $R''$ together with the atoms connecting them can form one or more rings.

Suitable olefins are 1-olefins, eg. ethylene, propylene, 1-butene, 1-pentene, 1-hexene, 4-methyl-1-pentene or 1-octene, styrene, dienes such as 1,3-butadiene, 1,4-hexadiene, vinylnorbornene, norbornadiene, ethylnorbornadiene and cyclic olefins such as norbornene, tetracyclododecene or methylnorbornene. In the process of the present invention, preference is given to homopolymerizing propylene or ethylene or copolymerizing propylene with ethylene and/or one or more 1-olefins having from 4 to 20 carbon atoms, eg. 1-butene or hexene, and/or one or more dienes having from 4 to 20 carbon atoms, eg. 1,4-butadiene, norbornadiene, ethylidenenorbornene or ethylnorbornadiene. Very suitable copolymers are ethylene-propylene copolymers, propylene-1-pentene copolymers and ethylene-propylene-1-butene, ethylene-propylene-1-pentene or ethylene-propylene-1,4-hexadiene terpolymers.

The polymerization is carried out at from −60° C. to 300° C., preferably from 50° C. to 200° C., very particularly preferably from 50° C. to 95° C. The pressure is from 0.5 to 2000 bar, preferably from 5 to 100 bar.

The polymerization can be carried out in solution, in bulk, in suspension or in the gas phase, continuously or batchwise, in one or more stages. As an example, impact copolymers are preferably produced in more than one stage. The homopolymer or random copolymer content of such a polymer can be produced in (a) first stage(s) and the copolymer rubber content can be produced in (a) consecutive stage(s).

The supported catalyst system prepared according to the present invention can be used as sole catalyst component for the polymerization of olefins or preferably in combination with at least one alkyl compound of elements of main Groups I to III of the Periodic Table, for example an aluminum alkyl, magnesium alkyl or lithium alkyl or an aluminoxane. The alkyl compound is added to the monomer or suspension medium and serves to free the monomer of substances, which can impair the catalytic activity. The amount of alkyl compound added depends on the quality of the monomers used.

To prepare olefin polymers having a broad or bimodal molecular weight distribution or a broad or bimodal melting range, it is recommended to use a catalyst system comprising two or more different metallocenes and/or two or more different cocatalysts. Alternatively two or more different catalyst systems of the present invention can be used as a mixture.

As molar mass regulator and/or to increase the activity, hydrogen is added if required.

The catalyst system may be supplied to the polymerization system as a solid or in the form of a paste or suspension in a hydrocarbon or may be treated with inert components, such as paraffins, oils, or waxes, to achieve better metering. If the catalyst system is to be metered into the reactor together with the monomer to be polymerized or the monomer mixture to be polymerized, the mixing unit and the metering line are preferably cooled.

Furthermore, an additive such as an antistatic or an alcohol can be used in the process of the present invention, for example to improve the particle morphology of the olefin polymer. In general it is possible to use all antistatics which are suitable in olefin polymerization processes. It is preferred to dose the antistatic directly into the polymerization system, either together with or separately from the catalyst system used.

The polymers prepared using the catalyst systems of the present invention display an uniform particle morphology and contain no fines. No agglomerates or deposits are obtained in the polymerization using the catalyst system of the present invention.

The catalyst systems of the present invention give polymers such as polypropylene having high molecular weight and cover a broad range of stereospecificity and regiospecificity.

The copolymers which can be prepared using the catalyst system based on metallocenes of formula 1 of the present invention have a significantly higher molar mass compared to the prior art. At the same time, such copolymers can be prepared using the catalyst system of the present invention at a high productivity and at industrially relevant process parameters without deposit formation.

The polymers prepared by the process of the present invention are suitable, in particular, for producing products such as fibers, filaments, injection-molded parts, films, sheets, caps, closures, bottles or large hollow bodies such as pipes with excellent properties.

EXAMPLES

The Examples below illustrate the invention. The comparative examples are presented for comparison purposes only and do not illustrate the invention.

General Procedures

The preparation and handling of the organometallic compounds were carried out under argon using Schlenk techniques or in a glove box. All solvents were purged with argon and dried over molecular sieves before use.

The metallocenes produced were characterized by $^1$H-NMR spectroscopy using a Bruker DMX 500 spectrometer, operating at 500 MHz using $CDCl_3$ as the solvent.

The polymers produced were characterized by $^1$H-NMR, $^{13}$C-NMR, DSC, GPC, TREF/ATREF, Melt Flow Rate and IR spectroscopy.

1. Gel Permeation Chromatography (GPC), Determination of Mw and Mw/Mn

A Waters Alliance/GPCV2000 equipped with a refractometer, a triple capillary on-line viscometer (Waters Corporation, 34 Maple Street, Milford, Mass., 01757 USA) and a light scattering detector PD 2040 (Precision Detectors Inc., 34 Williams Way, Bellingham, Mass., USA) was used for the determination of the molar mass data of the samples. 0.05 wt % solutions of the samples in 1,2,4-trichlorobenzene were analyzed at a temperature of 145° C. using a Mixed B light scattering quality column (Polymer Labs 1110-6100LS) and a Mixed B guard column (Polymer Labs 1110-1120). Weight average molar mass (Mw) and the ratio of weight average molar mass to number average molar mass (Mw/Mn) were calculated using the Cumulative Matching % Broad Standard procedure that is available in the Waters Millenium 3.2 GPC software module.

2. NMR Spectroscopy

Samples were prepared by weighing 0.32 g of polymer into 2.5 ml of a 1,2,4-trichlorobenzene/deuterobenzene-d6 (4:1 volume) mixture. Samples were heated to 125° C. and mixed until a homogeneous solution was formed (typically 1-4 hours). Spectra were obtained at 120° C. on a Varian Inova 500 instrument (Varian Inc., 3120 Hansen Way, Palo Alto, Calif., 94304, USA) operating at a $^{13}$C-spectrometer frequency of 125.7 MHz and using a 10 mm probe. Spectra were obtained using 5000 scans employing a π/2 pulse of 10.0 μs, a recycle delay of 10.0 s and an acquisition time of 2.5 s. Waltz-16 decoupling remained on throughout the pulse sequence to gain the signal to noise enhancement due to the effects of nOe. Spectra were processed with 1 Hz of line broadening. The mmmm peak in the methyl region of the spectrum was used as an internal chemical shift reference and was set to 21.85 ppm.

3. Differential Scanning Calorimetry (DSC), Determination of the Polymer Melting Point Tm DSC measurements were carried out using a Mettler Toledo DSC 822e (Mettler-Toledo Inc., 1900 Polaris. Parkway, Columbus, Ohio, 43240, USA). 4 mg of sample were weighed into a standard aluminum pan and subjected to the following temperature schedule:

The samples were heated from room temperature to 220° C. at a heating rate of 20° C./min, maintained at this temperature for 5 min, then cooled down to −55° C. at a cooling rate of 20° C./min, maintained at the same temperature for 5 min, then heated to 220° C. at a heating rate of 20° C./min. The melting point was determined from the second heating run as the temperature where the main peak was observed in the curve.

4. Analytical TREF (ATREF)

The TREF experiment is carried out on a TREF system built from a modified Waters 2000CV instrument (Waters Corporation, 34 Maple Street, Milford, Mass., 01757 USA). The 2000CV instrument is maintained at 140° C. in o-dichlorobenzene (ODCB) solvent at 1 ml/min flowrate. To detect the polyolefin fractions eluting from the TREF column, the system uses a heated infrared IR4 detector (PolymerChar Company, Valencia Technology Park, P.O. Box 176, Valencia, Va., E-46980, PATERNA, Spain). For cooling and heating of the TREF column, the system uses a temperature-programmable HAAKE Phoenix II oil bath (Thermo Electron Corporation, 401 Millcreek Road, Marietta, Ohio 45750, USA). The TREF separation column is a stainless steel column of 100 mm long and 0.75 mm diameter packed with 20-micrometer cross-linked polystyrene beads. This TREF column is maintained at the 140° C. temperature in the oil bath before the sample analyses. Polymer samples are dissolved in ODCB solvent at 140° C. at a concentration of 2 mg/ml. One ml of the test sample of the resultant ODCB solution is injected into the TREF column by the auto-injection system of the Waters 2000CV instrument with a flowrate of ODCB set at 1 ml/min. Following the sample injection, the ODCB flow is diverted away from the TREF column. As the sample is kept inside the column, the column is allowed to cool down in the oil bath from 140° C. down to 0° C. at the cooling rate of 1.5° C./min. In this cooling step, the polymer molecules in the test sample are precipitated onto the packing beads in the TREF column. While the column is still at 0° C. temperature, a flow of hot ODCB at 1 ml/min is re-introduced to the TREF column for 2 minutes to elute the soluble fraction of the polymer sample and detected by the IR detector set at 3.4 micrometer wavelength. Then, the temperature is raised at a heating rate of 2° C./min while the ODCB flow is maintained at 1 ml/min through the TREF column to elute the higher melting polymer fractions which are being detected on-line by the IR4 detector.

5. Melt Flow Rate (MFR)

The MFR of the samples were determined according to ISO 1133 at 230° C. Two different loads were used: 2.16 kg and 5 kg. Values are reported as MFR(230/2.16) and MFR (230/5), respectively.

6. Productivity

The productivity of a catalyst is determined by dividing the produced mass of polypropylene by the mass of catalyst used and the reaction time.

7. Yield

The yield of a sample is determined by dividing the isolated amount of the desired product divided by the theoretical achievable amount of the product.

The following abbreviations are employed:

PP=polypropylene

MC=metallocene

Cat=supported catalyst system h=hour

XS=Xylene Soluables

Synthesis of Metallocenes

Example 1

Dimethylsilanediylbis(2-methyl-4,7-bis-(4-t-butyl-phenyl)-indenyl)zirconium dichloride 4,7-Dibromo-2-methyl-indan-1-one

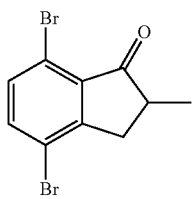

94.37 g (0.40 mol) 1,4-Dibromobenzene and 106.7 g (0.80 mol) anhydrous aluminum trichloride were placed in a 1000 ml round bottom flask equipped with a mechanical stirrer. 62.72 g (0.60 mol) 2-Methyl-acryloyl chloride were added under heat evolution (50-55° C.). The mixture was heated, starting at 105° C. a strong gas evolution was observed and the temperature rose to 135° C. Heating of the now solid mass was continued for 3 h at 110° C. After cooling to room temperature 200 g ice was added very carefully, followed by the careful addition of 200 ml conc. HCl. The mixture was extracted three times with 250 ml dichloromethane each. The combined organic layers were washed with 250 ml water and 250 ml of a saturated sodium bicarbonate solution, dried over magnesium sulfate, and the solvent was removed in vacuo. Flash chromatography using silica and heptane/dichloromethane (1:2) yielded 19.3 g (63 mmol, 16%) of the desired indanone as a white solid. $^1$H-NMR (500 MHz, CDCl3): δ=7.67, 7.54 (2×d, 2H, aromatic), 3.30 (m, 1H, COCHCH3), 2.74-2.64 (m, 2H, benzylic), 1.30 (d, 3H, CH$_3$) ppm.

4,7-Dibromo-2-methyl-1H-indene

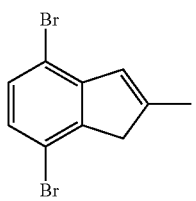

In a 250 ml round bottom flask 19.2 g (63 mmol) 4,7-Dibromo-2-methyl-indan-1-one were dissolved in 70 ml of toluene at 50° C. Then 2.63 g (1.1 eq.) sodium borohydride were added. At 50° C. 11 ml (4.3 eq.) methanol were added dropwise over a period of 30 min. Stirring was continued at 50° C. for 3 h (complete conversion) and then 50 ml water and 50 ml of 2M H$_2$SO$_4$ were added. The aqueous phase was extracted 2 times with 100 ml toluene. The combined organic layers were washed with 50 ml 2M H$_2$SO$_4$ and 50 ml of a sodium chloride solution, dried over magnesium sulfate and the solvent was removed in vacuo. 200 ml toluene and 200 mg p-toluene sulfonic acid were added and the solution was heated on a Dean-Stark-trap for 90 min. 50 ml of a saturated sodium bicarbonate solution were added. The aqueous layer was extracted 2 times with 50 ml toluene each. The combined organic layers were washed with 50 ml of a saturated sodium bicarbonate solution and 50 ml of a sodium chloride solution, dried over magnesium sulfate and the solvent was removed in vacuo to yield 17.8 g (62 mmol, 98%) of the desired indene as a slightly brown oil. $^1$H-NMR (500 MHz, CDCl3): δ=7.48, 7.35 (2×d, 2H, aromatic), 6.49 (s, 1H, indenyl-C=CH), 3.32 (s, 2H, benzylic), 2.12 (2, 3H, CH$_3$) ppm.

4,7-Bis-(4-t-butyl-phenyl)-2-methyl-1H-indene

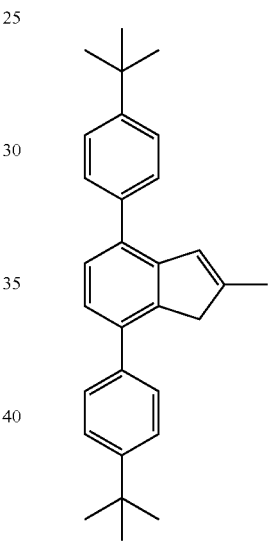

In a 250 ml roundbottom flask were placed 7.7 g (26.8 mmol) 4,7-Dibromo-2-methyl-1H-indene, 12.0 g (2.5 eq.) t-butylphenyl boronic acid, 120 mg (2 mol %) palladium acetate, 18.76 g (134.4 mmol) potassium carbonate, 17.24 g (53.5 mmol) tetrabutylammonium bromide, 74 ml degassed water and 74 ml degassed toluene. The mixture was stirred for 18 h at 76° C. After cooling to room temperature, 50 ml toluene and 50 ml water were added. The aqueous phase was extracted 3 times with 50 ml toluene. The combined organic layers were washed once with 100 ml of 2M sodium hydroxide solution and 3 times with 50 ml water each, and dried over magnesium sulfate. Removal of the solvent in vacuo and purification via flash chromatography on silica using heptane/dichloromethane (20:1) yielded 8.14 g (20.6 mmol, 77%) of the desired indene as a white solid. $^1$H-NMR (500 MHz, CDCl$_3$): δ=7.57-7.36 (m, 10H, aromatic), 6.70, 6.57 (2×s, 1H, indenyl-C=CH), 3.41 ("d", 2H, benzylic), 2.15 (2×s, 3H, CH₃), 1.37, 1.35 (2×s, 18H, C(CH₃)₃) ppm.

Bis-[4,7-bis-(4-t-butyl-phenyl)-2-methyl-1H-inden-1-yl]-dimethyl-silane

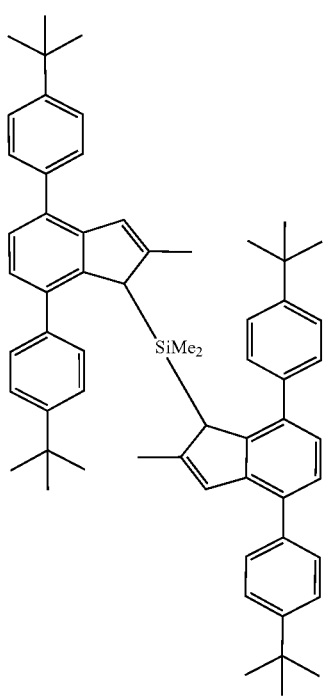

In a flame dried 250 ml roundbottom flask 7.45 g (18.9 mmol) 4,7-Bis-(4-t-butyl-phenyl)-2-methyl-1H-indene were dissolved 127 ml toluene and 7.45 ml THF. 7.93 ml (1.05 eq., 2.5 M in toluene) n-Butyl lithium were added dropwise at room temperature and the solution was heated to 80° C. for 1 h. After cooling to 50° C., 1.22 g (0.5 eq.) dimethyldichlorosilane were added and the reaction mixture was stirred for 17 h at 60° C. The mixture was given to 100 ml water. The aqueous phase was extracted 3 times with 50 ml toluene each and the combined organic layers were washed with 50 ml water and 50 ml of a saturated sodium chloride solution, and dried over magnesium sulphate. Removal of the solvent in vacuo and chromatography on silica using heptane/dichloromethane (10:1) as the eluent afforded 5.7 g (6.7 mmol, 71.4%) of the ligand as a slightly offwhite oil. ¹H-NMR (500 MHz, CDCl₃): δ=7.68-7.21 (m, 20H, aromatic), 6.84, 6.79 (1×d, 1×s, 2H, indenyl-C=CH), 3.85, 3.59 (1×m, 1×s, 2H, benzylic), 2.26, 2.19, 2.16, 2.15 (4×s, 6H, CH₃), 1.37-1.26 (m×s, 36H, C(CH₃)₃), 0.41, 0.27, 0.09, −0.11, −0.13 (5×s, 6H, Si(CH₃)₂) ppm.

Dimethylsilanediylbis(4,7-bis-(4-t-butyl-phenyl)-2-methyl-1-indenyl)zirconium dichloride In a flame dried 100 ml roundbottom flask 3.8 g (4.5 mmol) Bis-[4,7-bis-(4-t-butyl-phenyl)-2-methyl-1H-inden-1-yl]-dimethyl-silane were dissolved in 38 ml diethyl ether and 3.7 ml (2.05 eq., 2.5 M in toluene) n-butyl lithium were added at room temperature. After stirring overnight, 1.1 g (4.7 mmol) zirconium tetrachloride was added in portions. Stirring was continued for 5 h and the solid was isolated by filtration and washing twice with 15 ml diethyl ether each. The solid was extracted with 100 ml dichloromethane. Removal of the solvent in vacuo yielded 1.2 g (1.2 mmol, 27%) of the racemic complex. ¹H-NMR (500 MHz, CDCl₃): δ=7.80 (s, 2H, aromatic), 7.63, 7.51, 7.44 (3×m, 18H, aromatic), 6.99 (s, 2H, indenyl-C=CH), 2.31 (s, 6H, CH₃), 1.37 (s, 6H, Si(CH₃)₂), 1.36, 1.32 (2×s, 36H, C(CH₃)₃) ppm.

Example 2

Dimethylsilanediylbis(2-methyl-4,7-bis-(1-naphthyl)-indenyl)zirconium dichloride 4,7-Bis-(1-naphthyl)-2-methyl-1H-indene

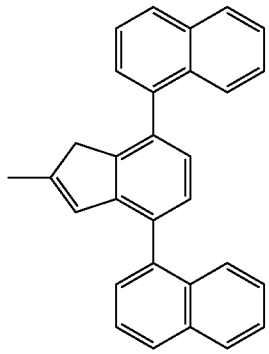

In a 500 ml roundbottom flask were placed 17.6 g (61.1 mmol) 4,7-Dibromo-2-methyl-1H-indene, 26.3 g (2.5 eq.) 1-napthyl boronic acid, 274 mg (2 mol %) palladium acetate, 42.23 g (2.5 eq.) potassium carbonate, 39.4 g (2 eq.) tetrabutylammonium bromide, 169 ml degassed water and 169 ml degassed toluene. The mixture was stirred under reflux for 20 h. After cooling to room temperature, 100 ml toluene and 100 ml water were added. The aqueous phase was extracted 3 times with 100 ml toluene. The combined organic layers were washed once with 100 ml of 2M sodium hydroxide solution and 3 times with 50 ml water each, and dried over magnesium sulfate. Removal of the solvent in vacuo and purification via flash chromatography on silica using heptane/dichloromethane (10:1) yielded 15.3 g (40 mmol, 65%) of the desired indene as a white solid. $^1$H-NMR (500 MHz, CDCl$_3$): δ=8.11, 7.89-7.77, 7.57-7.26 (3×m, 16H, aromatic), 6.61, 6.18 (2×s, 1H, indenyl-C=CH), 3.49 ("d", 2H, benzylic), 2.09 (2×s, 3H, CH$_3$) ppm.

Bis-[4,7-bis-(1-naphthyl)-2-methyl-1H-inden-1-yl]-dimethyl-silane

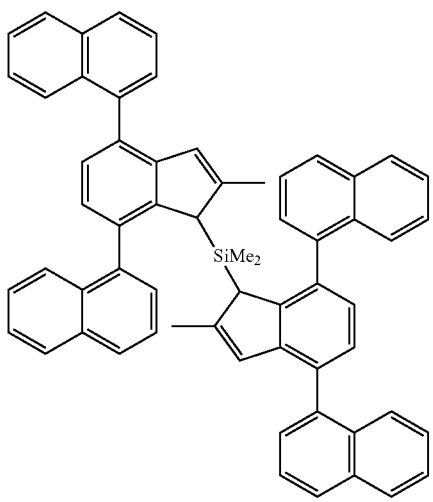

In a flame dried 250 ml roundbottom flask 2.0 g (5.2 mmol) 4,7-Bis-(1-naphthyl)-2-methyl-1H-indene were dissolved 34 ml toluene and 2 ml THF. 2.2 ml (1.05 eq., 2.5 M in toluene) n-Butyl lithium were added dropwise at room temperature and the solution was heated to 80° C. for 1 h. After cooling to 50° C., 337 mg (0.5 eq.) dimethyldichlorosilane were added and the reaction mixture was stirred for 17 h at 60° C. The mixture was given to 100 ml water. The aqueous phase was extracted 3× with 50 ml toluene each and the combined organic layers were washed with 50 ml water and 50 ml of a saturated sodium chloride solution, and dried over magnesium sulphate. Removal of the solvent in vacuo and chromatography on silica using heptane/dichloromethane (10:1) as the eluent afforded 1.8 g (2.2 mmol, 84%) of the ligand as a slightly offwhite oil. $^1$H-NMR (500 MHz, CDCl$_3$): =8.08-7.29 (m, 32H, aromatic), 6.35, 6.26 (2×d, 2H, indenyl-C=CH), 4.04-3.94 (m, 2H, benzylic), 2.24-2.15 (m, 6H, CH$_3$), 0.00, −0.01, −0.02, −0.03, −0.04 (5×s, 6H, Si(CH$_3$)$_2$) ppm.

Dimethylsilanediylbis(4,7-bis-(1-naphthyl)-2-methyl-1-indenyl)zirconium dichloride

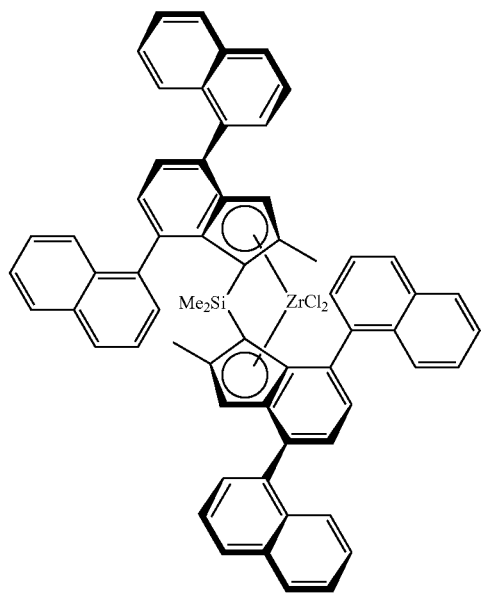

In a flame dried 100 ml roundbottom flask 1.8 g (2.2 mmol) Bis-[4,7-bis-(1-naphthyl)-2-methyl-1H-inden-1-yl]-dimethyl-silane were dissolved in 18 ml diethyl ether and 1.8 ml (2.05 eq., 2.5 M in toluene) n-butyl lithium were added at room temperature. After stirring overnight, 536 mg (2.3 mmol) zirconium tetrachloride was added in portions. Stirring was continued for 2 h and the solvent was removed in vacuo. 30 ml toluene and 1.8 ml THF were added and the mixture was stirred for 4 h at 75° C. The solvent was removed and the complex was isolated by extraction with toluene to yield 430 mg (0.44 mmol, 20%) of the racemic complex. $^1$H-NMR (500 MHz, CDCl$_3$): δ=8.04-7.11 (m, 32H, aromatic), 6.65 (s, 2H, indenyl-C=CH), 2.21 (s, 6H, CH$_3$), 1.27 (s, 6H, Si(CH$_3$)$_2$) ppm.

Comparative Example 3

Bis(2,4,7-trimethyl-1H-inden-1-yl)-dimethyl-silane

Bis(2,4,7-trimethyl-1H-inden-1-yl)-dimethyl-silane 10.6 ml (26.5 mmole) of a 2.5 M n-butyl lithium solution in hexane were added to a solution of 4.2 g (26.5 mmole) of 2,4,7-trimethylindene in 50 ml of tetrahydrofuran at 0° C. and the mixture was heated under reflux for a further hour and then added to a solution of 3.42 g of dimethyldichlorosilane in 12 ml of tetrahydrofuran at room temperature. The red suspension was stirred at room temperature for 4 hours and was heated under reflux for additional 4 hours. The mixture was poured onto ice and extracted with diethylether. The combined organic phases were dried over sodium sulfate and evaporated to dryness. Recrystallization from hexane yielded 3.95 g (10.6 mmole) of Bis(2,4,7-trimethyl-1H-inden-1-yl]-dimethylsilane.

Comparative Example 4

Dimethylsilanediylbis(2,4,7-trimethyl-indenyl)-zirconiumdichloride

Dimethylsilanediylbis(2,4,7-trimethyl-indenyl)-zirconiumdichloride

Continuing with the product produced in Comparative Example 3, 4.32 ml (10.8 mmole) of a 2.5 M n-butyl lithium solution in hexane were added to a solution of 2.0 g (5.4 mmole) of Bis(2,4,7-trimethyl-1H-inden-1-yl]-dimethylsilane in 40 ml of diethylether at 0° C. The mixture was stirred at room temperature for 2 hours and concentrated to 25 ml and the precipitate was filtered over a G4 frit. After being washed with hexane the dilithium salt was added to 1.26 g (5.4 mmole) of zirconiumtetrachloride in 25 ml of methylene chloride at −78° C. The solvent was removed in vacuum resulting in a crude metallocene with a rac:meso ratio of 1:1. Purification and rac:meso separation was accomplished by fractional crystallisation from methylenehloride/hexane.

Preparation of Methylaluminoxane Treated Silica

Example 5

To a stirred suspension of 293 g of silica (Grace XPO2107, dried at 180° C. and 1 mbar for 16 hours, LOD<0.5 wt % and LOI=2.6 wt %) in 1500 mL of toluene is added slowly 300 mL of a 30 wt-% solution of methylaluminoxane in toluene (Albemarle Corporation) at room temperature. During the addition the temperature must not exceed 30° C. After the addition is complete, the mixture is stirred for two hours at room temperature and separated by filtration. The residue is washed with two 1500 mL portions of toluene and three 1500 mL portions of isohexane and dried in vacuum to constant weight. The methylaluminoxane treated silica is obtained as a free-flowing powder in a yield of 408 g.

Preparation of Supported Metallocene Catalysts

Example 6

10.0 g of the methylaluminoxane treated silica prepared in Example 5 are placed in a fitted glass filter as a column with a smooth surface. A minimal amount of toluene is added and the treated silica is carefully stirred with a spatula to remove any air pockets in the column. The excess toluene is removed by filtration leaving a smooth surface. In a separate flask 361 mg of Dimethylsilanediylbis(2-methyl-4,7-bis-(4-t-butyl-phenyl)-1-indenyl)zirconium dichloride (prepared in Example 1) are mixed with 27 mL of toluene and 13.6 mL of a 30 wt-% solution of methylaluminoxane in toluene (Albemarle Corporation). The slurry is stirred at room temperature for one hour to give an orange solution. This solution is then carefully added on top of the methylaluminoxane treated silica and slowly filtered off within approximately 30 minutes. When the surface of the colored solution reaches the top of the silica, the filtration process is stopped and the filter cake is carefully and thoroughly stirred by means of a spatula. The catalyst is then allowed to rest for one hour. The residual solvent is filtered off and the catalyst is washed twice with isohexane (20 mL) and dried in a nitrogen purge to constant weight. The catalyst is obtained as free-flowing reddish powder in a yield of 11.8 g.

Example 7

10.0 g of the methylaluminoxane treated silica prepared in Example 5 are placed in a flitted glass filter as a column with a smooth surface. A minimal amount of toluene is added and the treated silica is carefully stirred with a spatula to remove any air pockets in the column. The excess toluene is removed by filtration leaving a smooth surface. In a separate flask 353 mg of Dimethylsilanediylbis(2-methyl-4,7-bis-(1-naphthyl)-indenyl)zirconium dichloride (prepared in Example 2) are mixed with 27 mL of toluene and 13.6 mL of a 30 wt-% solution of methylaluminoxane in toluene (Albemarle Corporation). The slurry is stirred at room temperature for one hour to give an orange solution. This solution is then carefully added on top of the methylaluminoxane treated silica and slowly filtered off within approximately 30 minutes. When the surface of the colored solution reaches the top of the silica, the filtration process is stopped and the filter cake is carefully and thoroughly stirred by means of a spatula. The catalyst is then allowed to rest for one hour. The residual solvent is filtered off and the catalyst is washed twice with isohexane (20 mL) and dried in a nitrogen purge to constant weight. The catalyst is obtained as free-flowing reddish powder in a yield of 11.5 g.

Comparative Example 8

10.0 g of the methylaluminoxane treated silica prepared in Example 12 are placed in a fritted glass filter as a column with a smooth surface. A minimal amount of toluene is added and the treated silica is carefully stirred with a spatula to remove any air pockets in the column. The excess toluene is removed by filtration leaving a smooth surface. In a separate flask 191 mg of Dimethylsilanediylbis(2,4,7-trimethyl-indenyl)-zirconiumdichloride (prepared in Comparative Example 4) are mixed with 27 mL of toluene and 13.6 mL of a 30 wt-% solution of methylaluminoxane in toluene (Albemarle Corporation). The slurry is stirred at room temperature for one hour to give an orange solution. This solution is then carefully added on top of the methylaluminoxane treated silica and slowly filtered off within approximately 30 minutes. When the surface of the colored solution reaches the top of the silica, the filtration process is stopped and the filter cake is carefully and thoroughly stirred by means of a spatula. The catalyst is then allowed to rest for one hour. The residual solvent is filtered off and the catalyst is washed twice with isohexane (20 mL) and dried in a nitrogen purge to constant weight. The catalyst is obtained as free-flowing orange powder in a yield of 11.5 g.

Polymerizations

Polymerization Procedure (Batch Propylene Homo- and Co-Polymerization)

A dry and nitrogen purged 5 dm$^3$ autoclave equipped with a stirrer is charged with if desired 100 g of metallocene polymer seed bed. Optionally, a certain amount of hydrogen is metered in. Triisobutylaluminum (1 cm$^3$ of a 10 wt.-% solution in heptane), liquid propylene (one-half of the total amount used for the run), and optionally, a certain amount of ethylene are metered in and the mixture is stirred for at least 5 minutes (stirrer speed 200 rpm) at 20° C. Then supported metallocene catalyst, suspended in 5 cm$^3$ of white oil, is injected with liquid propylene (one-half of total amount used for the run). The reactor is heated to the internally measured run temperature (65, 60 or 30° C.) within 11 minutes. The polymerization reaction is allowed to proceed at the run temperature for either 15 or 60 minutes. During the 60 min copolymerization runs the reactor pressure was maintained by continuous feeding of ethylene and propylene. The polymerization is stopped by releasing the monomer and cooling down the reactor. The polymer is discharged and dried under reduced pressure.

The following examples were carried out according to the polymerization procedure described above:

Propylene Homo Polymers

Analysis 1: Production of Propylene Homo Polymers without the Use of Hydrogen.

Table 3 shows the results of two experimental Metallocene catalysts conforming to the requirements of the invention compared to a comparative example.

The individual catalyst comparisons between inventive examples 1 and 5 and comparative example 9 substantiate the outstanding improvements over the state of the art. When examples 1 and 5 are compared to comparative example 9, the inventive examples exhibit significantly lower MFR 2.16 rates and increases in Molecular Weight and Polymer Melting Point ($T_m$). Specifically for MFR 2.16, the inventive examples 1 and 5 show MFR values of less than 0.2 while the MFR of the polymer produced in the comparative example 9 is so high that the MFR was out of range and was not measureable. For the Polymer Melting Point ($T_m$), the inventive examples 1 and 5 show a respective increase of 3° C. over the original value. For the molecular weight, the inventive

TABLE 1

Polymerizations

| Poly. Example | Catalyst From Example | H2 [mg] | C3 [g] | C2 [g] | Catalyst [mg] | Polym. Temp. [° C.] | Polym. Time [min] | Yield [g] | Productivity [g polymer/g catalyst*hour] |
|---|---|---|---|---|---|---|---|---|---|
| 1 | 6 | — | 1830 | — | 68 | 65 | 60 | 119 | 1750 |
| 2 | 6 | 50 | 1834 | — | 52 | 65 | 60 | 692 | 13300 |
| 3 | 6 | 10 | 1836 | 20 | 75 | 65 | 60 | 210 | 2800 |
| 4 | 6 | 10 | 1767 | 60 | 75 | 65 | 60 | 233 | 3100 |
| 5 | 7 | — | 1838 | — | 110 | 65 | 60 | 132 | 1200 |
| 6 | 7 | 50 | 1834 | — | 56 | 65 | 60 | 532 | 9500 |
| 7 | 7 | 10 | 1756 | 20 | 60 | 65 | 60 | 117 | 1950 |
| 8 | 7 | 10 | 1780 | 60 | 60 | 65 | 60 | 172 | 2870 |
| 9 | 8 | — | 1836 | — | 60 | 65 | 60 | 62 | 1033 |
| 10 | 8 | 50 | 1832 | — | 58 | 65 | 60 | 412 | 7100 |
| 11 | 8 | 10 | 1820 | 20 | 62 | 65 | 60 | 90 | 1450 |
| 12 | 8 | 10 | 1824 | 60 | 60 | 65 | 60 | 107 | 1780 |

TABLE 2

Polymer Properties

| Poly. Example | Catalyst from Example | C2 [wt %] | Tm [deg C.] | MFR 2.16 [g/10'] | Mw [kg/mol] | Mw/Mn | XS [wt %] |
|---|---|---|---|---|---|---|---|
| 1 | 6 | — | 147 | 0.2 | 817 | 2.3 | 1.4 |
| 2 | 6 | — | 149 | 16.3 | 207 | 2.3 | 1.1 |
| 3 | 6 | 2.2 | 135 | 8.5 | 289 | 2.0 | 1.4 |
| 4 | 6 | 5.2 | 113 | 10.0 | 237 | 2.2 | 1.6 |
| 5 | 7 | — | 147 | 0.01 | 1420 | 2.4 | 1.4 |
| 6 | 7 | — | 148 | 3.3 | 330 | 2.5 | 1.1 |
| 7 | 7 | 2.5 | 130 | 5.9 | 309 | 2.7 | 1.4 |
| 8 | 7 | 5.5 | 111 | 7.9 | 295 | 2.5 | 1.7 |
| 9 | 8 | — | 144 | out of measureable range | 73 | 2.6 | n.d |
| 10 | 8 | — | 146 | out of measureable range | 19 | 2.7 | n.d |
| 11 | 8 | | | Sticky waxy material | | | |
| 12 | 8 | | | Sticky waxy material | | | |

Analysis of Results

Table 1 and Table 2 represent the raw data presented by test run; the remaining tables 3-break that data out by the ratio of propylene to ethylene (or if it is a propylene homo polymer) and whether hydrogen was used in the polymerization process.

examples 1 and 5 show a respective increase of more than 10 to 20 fold over the original value. This dramatic increase of Molecular Weight opens full access to application fields like film, pipe or sheets, where a high Molecular Weight is mandatory. Even more surprisingly is that the inventive examples showed these dramatic improvements in product properties at much higher productivity levels. Inventive example 1 shows a 69% increase in productivity and inventive example 5 shows a 16% increase in productivity over the original value.

Analysis 2: Production of Propylene Homo Polymers with the Use of Hydrogen.

Table 4 shows the results of two experimental Metallocene catalysts conforming to the requirements of the invention compared to a comparative example.

The individual catalyst comparisons between inventive examples 2 and 6 and comparative example 10 again substantiate the outstanding improvements over the state of the art. When examples 2 and 6 are compared to comparative example 10, the inventive examples exhibit significantly lower MFR 2.16 rates and increases in Molecular Weight and Polymer Melting Point ($T_m$). Specifically for MFR 2.16, the inventive examples 2 and 6 show MFR values of less than 16.3 while the MFR of the polymer produced in the comparative example 10 is so high that the MFR was out of range and was not measureable. For the Polymer Melting Point ($T_m$), the inventive examples 2 and 6 show a respective increase of 2 to 3° C. over the original value. For the molecular weight, the inventive examples 2 and 6 show a respective increase of more than 10 to 17 fold over the original value. This dramatic increase of Molecular Weight opens full access to application fields like film, fibre and injection moulding, where a Molecular Weight in the achieved range is mandatory. Even more surprisingly is that the inventive examples showed these dramatic improvements in product properties at much higher productivity levels. Inventive example 2 shows a 87% increase in productivity and inventive example 6 shows a 34% increase in productivity over the original value.

Propylene/Ethylene Co-Polymers

The polymerization performance and the properties of products made from the inventive catalysts were tested at two levels of an ethylene/propylene mix to form co-polymers (Table 5). In each case the inventive catalysts from examples 6 and 7 have been tested, and compared against the comparative catalyst from example 8.

Analysis 3: Production of Propylene/Ethylene Co-Polymers with a Propylene/Ethylene Ratio of Approximately 90 and 30 (20 g Resp. 60 g of Ethylene) in the Presence of Hydrogen.

Two inventive catalyst (examples 3, 4 and 7, 8) have tested against the comparative catalyst, (examples 11, 12), the results being presented in Table 5. As before, the inventive catalyst showed significant improvements over the comparative catalyst. Under the applied standard conditions for testing random co-polymers and using the comparative catalyst it was no longer possible to produce a polymer! The product isolated from the polymerisation was a waxy and sticky material. As a consequence, such a catalyst can not be commercially used. Specifically for MFR 2.16, the inventive examples 3, 4 and 7, 8 show MFR values of still less than 10 while the MFR of the waxes (as indicated above, the material was no longer a polymer!) produced in the comparative examples 11 and 12 was so high that the MFR was out of range and was not measureable. For the molecular weight, the inventive examples 3, 4 and 7, 8 show still values above 230 kg/mol which open full access to application fields like high transparent film, fibre and high transparent injection moulding. Even more surprisingly is that the inventive examples showed these dramatic improvements in product properties at much higher productivity levels. Inventive examples 3 and 7 where 20 g of ethylene was used in the polymerization show a 93% and 34% increase in productivity over the directly comparable value of example 11 and inventive examples 4 and 8 where 60 g of ethylene was used show a 74% and 61% increase in productivity over the directly comparable value of example 12.

While the above description contains many specifics, these specifics should not be construed as limitations of the invention but merely as preferred embodiments thereof. Those skilled in the art will envision many other embodiments within the scope and spirit of the claims as defined by the claims appended hereto.

TABLE 3

Production of propylene homo polymers without the use of hydrogen

| Poly. Example | Catalyst From Example | H2 [mg] | C3 [g] | C2 [g] | Catalyst [mg] | Polym. Temp. [° C.] | Polym. Time [min] | Yield [g] | Productivity [g polymer/g catalyst*hour] | Tm [deg C.] | MFR 2.16 [g/10'] | Mw [kg/mol] | Mw/Mn | XS [wt %] |
|---|---|---|---|---|---|---|---|---|---|---|---|---|---|---|
| 1 | 6 | — | 1830 | — | 68 | 65 | 60 | 119 | 1750 | 147 | 0.2 | 817 | 2.3 | 1.4 |
| 5 | 7 | — | 1838 | — | 110 | 65 | 60 | 132 | 1200 | 147 | 0.01 | 1420 | 2.4 | 1.4 |
| 9 | 8 | — | 1836 | — | 60 | 65 | 60 | 62 | 1033 | 144 | out of measureable range | 73 | 2.6 | n.d |

TABLE 4

Production of propylene homo polymers with the use of hydrogen

| Poly. Example | Catalyst From Example | H2 [mg] | C3 [g] | C2 [g] | Catalyst [mg] | Polym. Temp. [° C.] | Polym. Time [min] | Yield [g] | Productivity [g polymer/g catalyst*hour] | Tm [deg C.] | MFR 2.16 [g/10'] | Mw [kg/mol] | Mw/Mn | XS [wt %] |
|---|---|---|---|---|---|---|---|---|---|---|---|---|---|---|
| 2 | 6 | 50 | 1834 | — | 52 | 65 | 60 | 692 | 13300 | 149 | 16.3 | 207 | 2.3 | 1.1 |
| 6 | 7 | 50 | 1834 | — | 56 | 65 | 60 | 532 | 9500 | 148 | 3.3 | 330 | 2.5 | 1.1 |
| 10 | 8 | 50 | 1832 | — | 58 | 65 | 60 | 412 | 7100 | 146 | out of measureable range | 19 | 2.7 | n.d |

TABLE 5

Production of propylene/ethylene co-polymers with a propylene/ethylene ratio of approximately 90 and 30 (20 g resp. 60 g of ethylene) in the presence of hydrogen

| Poly. Example | Catalyst From Example | H2 [mg] | C3 [g] | C2 [g] | Catalyst [mg] | Polym. Temp. [° C.] | Polym. Time [min] | Yield [g] | Productivity [g polymer/g catalyst* hour] | C2 [wt %] | Tm [deg C.] | MFR 2.16 [g/10'] | Mw [kg/mol] | Mw/Mn | XS [wt %] |
|---|---|---|---|---|---|---|---|---|---|---|---|---|---|---|---|
| 3  | 6 | 10 | 1836 | 20 | 75 | 65 | 60 | 210 | 2800 | 2.2 | 135 | 8.5  | 289 | 2.0 | 1.4 |
| 4  | 6 | 10 | 1767 | 60 | 75 | 65 | 60 | 233 | 3100 | 5.2 | 113 | 10.0 | 237 | 2.2 | 1.6 |
| 7  | 7 | 10 | 1756 | 20 | 60 | 65 | 60 | 117 | 1950 | 2.5 | 130 | 5.9  | 309 | 2.7 | 1.4 |
| 8  | 7 | 10 | 1780 | 60 | 60 | 65 | 60 | 172 | 2870 | 5.5 | 111 | 7.9  | 295 | 2.5 | 1.7 |
| 11 | 8 | 10 | 1820 | 20 | 62 | 65 | 60 | 90  | 1450 |     |     | Sticky waxy material | | | |
| 12 | 8 | 10 | 1824 | 60 | 60 | 65 | 60 | 107 | 1780 |     |     | Sticky waxy material | | | |

What is claimed is:

1. A catalyst composition comprising a metallocene compound having formula 1:

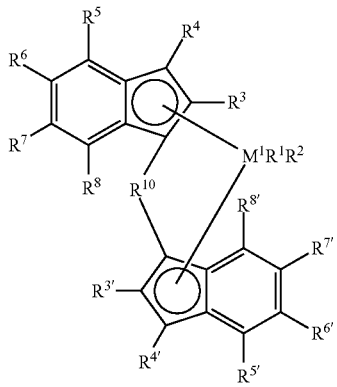

in which:

$M^1$ is a metal of the Groups 4-6 of the Periodic Table of the Elements, $R^1$ and $R^2$ are identical or different and are each a hydrogen atom, an alkyl group of from 1 to about 10 carbon atoms, an alkoxy group of from 1 to about 10 carbon atoms, an aryl group of from 6 to about 20 carbon atoms, an aryloxy group of from 6 to about 10 carbon atoms, an alkenyl group of from 2 to about 10 carbon atoms, an OH group, a halogen atom, or a $NR_2^{32}$ group, where $R^{32}$ is an alkyl group of from 1 to about 10 carbon atoms or an aryl group of from 6 to about 14 carbon atoms and $R^1$ and $R^2$ may form one or more ring system(s), $R^3$ and $R^{3'}$ are identical or different and are each a halogen atom, or a linear, cyclic or branched hydrocarbon group which may optionally be halogenated and/or may contain one or more hetero atoms selected from Si, B, Al, O, S, N and P, said hydrocarbon group being selected from an alkyl group of from 1 to about 20 carbon atoms, an alkylalkenyl group of from 3 to about 20 carbon atoms, an alkylaryl group of from 7 to about 40 carbon atoms, an alkylarylalkenyl group of from 9 to about 40 carbon atoms, an arylalkyl group of 7 to 20 carbon atoms, an alkoxy group of from 1 to about 10 carbon atoms, an aryl group of from 6 to about 20 carbon atoms, a heteroaryl group of 3 to about 20 carbon atoms, an aryloxy group of from 6 to about 10 carbon atoms, a silyloxy group of about 3 to 20 carbon atoms, an alkenyl group of from 2 to about 10 carbon atoms and a $NR_2^{32}$ group, where $R^{32}$ is an alkyl group of from 1 to about 10 carbon atoms or an aryl group of from 6 to about 14 carbon atoms, $R^4$ and $R^{4'}$ are identical or different and are each a hydrogen atom, a halogen atom, or a linear, cyclic or branched hydrocarbon group which may be halogenated and/or may contain one or more hetero atoms selected from Si, B, Al, O, S, N and P, said hydrocarbon group being selected from an alkyl group of from 1 to about 20 carbon atoms, an alkylalkenyl group of from 3 to about 20 carbon atoms, an alkylaryl group of from 7 to about 40 carbon atoms, or an alkylarylalkenyl group of from 9 to about 40 carbon atoms, an arylalkyl group of 7 to 20 carbon atoms, an alkoxy group of from 1 to about 10 carbon atoms, an aryl group of from 6 to about 20 carbon atoms, a heteroaryl group of 3 to about 20 carbon atoms, an aryloxy group of from 6 to about 10 carbon atoms, a silyloxy group of about 3 to 20 carbon atoms, an alkenyl group of from 2 to about 10 carbon atoms, a halogen atom and a $NR_2^{32}$ group, where $R^{32}$ is an alkyl group of from 1 to about 10 carbon atoms or an aryl group of from 6 to about 14 carbon atoms, $R^5$, $R^{5'}$, $R^8$ and $R^{8'}$ are identical or different and are each an aryl group of from 6 to about 40 carbon atoms, an alkylaryl group of from 7 to about 40 carbon atoms, an alkenylaryl group of from 8 to about 40 carbon atoms, a substituted or unsubstituted silylaryl group, or an (alkyl)(silyl)aryl group, and optionally may be halogenated and/or may contain one or more hetero atoms selected from Si, B, Al, O, S, N and P, $R^6$, $R^{6'}$, $R^7$ and $R^{7'}$ are identical or different and are each a hydrogen atom, a halogen, or a linear, cyclic or branched hydrocarbon group which may optionally be halogenated and/or may contain one or more hetero atoms selected from Si, B, Al, O, S, N and P, wherein the hydrocarbon group is selected from an alkyl group of from 1 to about 20 carbon atoms, an alkylalkenyl group of from 3 to about 20 carbon atoms, an alkylaryl group of from 7 to about 40 carbon atoms, an alkylarylalkenyl group of from 9 to about 40 carbon atoms, an arylalkyl group of 7 to 20 carbon atoms, an alkoxy group of from 1 to about 10 carbon atoms, an aryl group of from 6 to about 20 carbon atoms, a heteroaryl group of 3 to about 20 carbon atoms, an aryloxy group of from 6 to about 10 carbon atoms, a silyloxy group of about 3 to 20 carbon atoms, an alkenyl group of from 2 to about 10 carbon atoms, a halogen atom and a $NR_2^{32}$ group, where $R^{32}$ is an alkyl group of from 1 to about 10 carbon atoms or an aryl group of from 6 to about 14 carbon atoms, $R^{10}$ is a bridging group wherein $R^{10}$ is selected from:

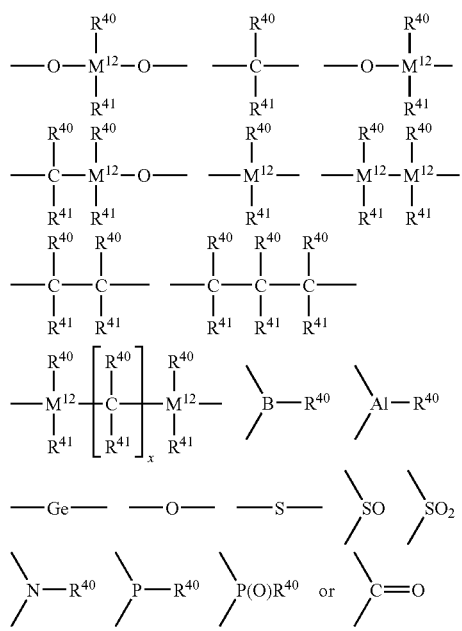

where $R^{40}$ and $R^{41}$, even when bearing the same index, can be identical or different and are each a hydrogen atom, or a hydrocarbon group which may optionally be halogenated or which may contain hetero atoms selected from Si, B, Al, O, S, N and P, wherein the hydrocarbon group is selected from an alkyl group having from 1 to about 30 carbon atoms, an aryl group of from 6 to about 40 carbon atoms, a fluoroalkyl group of from 1 to about 10 carbon atoms, an alkoxy group of from 1 to about 10 carbon atoms, an aryloxy group of from 6 to about 10 carbon atoms, an alkenyl group of from 2 to about 10 carbon atoms, an arylalkyl group of from 7 to about 40 carbon atoms, an alkylaryl group of from 7 to about 40 carbon atoms, a substituted or unsubstituted alkylsilyl, alkyl(aryl)silyl group, an arylsilyl group or an arylalkenyl group of from 8 to about 40 carbon atoms, or wherein $R^{40}$ and $R^{41}$ together with the atoms connecting them can form one or more cyclic systems, x is an integer from 1 to 18, $M^{12}$ is silicon, germanium or tin, and $R^{10}$ may also link two units of the formula 1 to one another.

2. The catalyst composition of claim 1 wherein:

$M^1$ is a metal of the Group 4 of the Periodic Table of the Elements, $R^1$ and $R^2$ are identical or different and are each an alkyl group of from 1 to about 10 carbon atoms, an alkoxy group of from 1 to about 10 carbon atoms, an aryloxy group of from 6 to about 10 carbon atoms or a halogen atom, or $R^1$ and $R^2$ together may form one or more ring system(s), $R^3$ and $R^{3'}$ are identical or different and are each a halogen atom or a linear, cyclic or branched hydrocarbon group which may optionally be halogenated and/or may optionally contain one or more hetero atoms selected from Si, B, Al, O, S, N and P, wherein the hydrocarbon group is selected from an alkyl group of from 1 to about 10 carbon atoms, an alkylalkenyl group of from 3 to about 10 carbon atoms, an alkylaryl group of from 7 to about 20 carbon atoms, an alkylarylalkenyl group of from 9 to about 20 carbon atoms, an arylalkyl group of 7 to 15 carbon atoms, an alkoxy group of from 1 to about 6 carbon atoms, an aryl group of from 6 to about 10 carbon atoms, a heteroaryl group of 3 to about 10 carbon atoms, an aryloxy group of from 6 to about 10 carbon atoms, a silyloxy group of about 3 to 10 carbon atoms, an alkenyl group of from 2 to about 6 carbon atoms and a $NR_2^{32}$ group where $R^{32}$ is an alkyl group of from 1 to about 10 carbon atoms or an aryl group of from 6 to about 10 carbon atoms, $R^4$ and $R^{4'}$ are identical or different and are each a hydrogen atom, or an alkyl group of from 1 to about 20 carbon atoms which may optionally be halogenated and/or may optionally contain one or more hetero atoms selected from Si, B, Al, O, S, N and P, $R^5$, $R^{5'}$, $R^8$ and $R^{8'}$ are identical or different and are each an aryl group of from 6 to about 40 carbon atoms, an alkylaryl group of from 7 to about 40 carbon atoms, and may optionally contain one or more hetero atoms selected from B, Al, O, S, N, P, F, Cl and Br, $R^6$, $R^{6'}$, $R^7$ and $R^{7'}$ are identical or different and are each a hydrogen atom, or an alkyl group of from 1 to about 20 carbon atoms which may be halogenated and/or may contain one or more hetero atoms selected from B, Al, O, S, N and P, $R^{10}$ is $R^{40}R^{41}Si=$, $R^{40}R^{41}Ge=$, $R^{40}R^{41}C=$ or $-(R^{40}R^{41}C-CR^{40}R^{41})-$, where $R^{40}$ and $R^{41}$ are identical or different and are each a hydrogen atom, a hydrocarbon group of from 1 to about 30 carbon atoms, in particular an alkyl group of from 1 to about 10 carbon atoms, an aryl group of from 6 to about 40 carbon atoms, an arylalkyl group of from 7 to about 14 carbon atoms, or an alkylaryl group of from 7 to about 14 carbon atoms.

3. The catalyst composition of claim 1 wherein:

$M^1$ is zirconium, $R^1$ and $R^2$ are identical and are methyl, chlorine or phenolate, $R^3$ and $R^{3'}$ are identical and are a linear, cyclic or branched hydrocarbon group selected from methyl, ethyl, n-propyl, i-propyl, cyclopropyl, n-butyl, t-butyl, t-butyl-methyl, i-butyl, s-butyl, n-pentyl, n-hexyl, n-heptyl, n-octyl, n-nonyl, n-decyl, cyclopropyl-methyl, cyclopentyl, cyclopentyl-methyl, cyclohexyl, cyclohexyl-methyl, (1-adamantyl)methyl, (2-adamantyl)methyl, benzyl, phenylethyl and phenyl-propyl, $R^4$ and $R^{4'}$ are identical and are each a hydrogen atom, $R^5$, $R^{5'}$, $R^8$ and $R^{8'}$ are identical and are each an aryl group of from 6 to about 20 carbon atoms, selected from phenyl, 1-naphtyl, 2-naphtyl, an alkylaryl group of from 7 to about 40 carbon atoms which may optionally contain one or more hetero atoms selected from B, Al, O, S, N, P, F, Cl and Br, the alkylaryl group being selected from 4-methyl-phenyl, 4-ethyl-phenyl, 4-i-propyl-phenyl, 4-t-butyl-phenyl, 3,5-dimethylphenyl, 3,5-di-t-butyl-4-methoxy-phenyl, and 2,3,4,5,6-pentafluorophenyl, $R^6$, $R^{6'}$, $R^7$ and $R^{7'}$ are identical and are each a hydrogen atom, the bridging unit $R^{10}$ is $R^{40}R^{41}Si=$ or $R^{40}R^{41}Ge=$, where $R^{40}$ and $R^{41}$ are identical or different and are methyl, ethyl, propyl, butyl, pentyl, hexyl, heptyl, octyl, nonyl, decyl, undecyl, dodecyl, cyclopentyl, cyclopentadienyl, cyclohexyl, phenyl, naphthyl, benzyl, or 3,3,3-trifluoropropyl.

4. The catalyst composition of claim 1 wherein,
$M^1$ is zirconium,
$R^1$ and $R^2$ are identical and are methyl or chlorine,
$R^3$ and $R^{3'}$ are identical and are each methyl, n-heptyl, n-octyl, n-nonyl, n-decyl, cyclohexyl-methyl, t-butyl-methyl, (1-adamantyl)methyl, (2-adamantyl)methyl, benzyl, phenethyl or phenyl-propyl,
$R^4$ and $R^{4'}$ are identical and are each a hydrogen atom,
$R^5$, $R^{5'}$, $R^8$ and $R^{8'}$ are identical and are each phenyl, 1-naphthyl, 2-naphtyl, 4-methyl-phenyl, 4-ethyl-phenyl, 4-i-propyl-phenyl, 4-t-butyl-phenyl, 3,5-dimethylphenyl, 3,5-di-t-butyl-4-methoxy-phenyl, 2,3,4,5,6-pentafluorophenyl,
$R^6$, $R^{6'}$, $R^7$ and $R^{7'}$ are identical and are each a hydrogen atom the bridging unit $R^{10}$ is $R^{40}R^{41}Si=$ or $R^{40}R^{41}Ge=$, where $R^{40}$ and $R^{41}$ are identical or different and are methyl, ethyl, propyl, butyl, pentyl, hexyl, heptyl, octyl, nonyl, decyl, undecyl, dodecyl, cyclopentyl, cyclopentadienyl, cyclohexyl, phenyl, naphthyl, benzyl, or 3,3,3-trifluoropropyl.

5. The catalyst composition of claim 1 further including an aluminoxane, a Lewis acid or an ionic compound capable of converting the metallocene compound to a cationic compound.

6. The catalyst composition of claim 5 wherein the aluminoxane is a compound having the general formula selected from one of formulas 6, 7, 8, or 9:

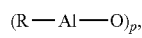  (Formula 6)

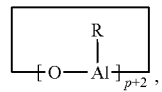  (Formula 7)

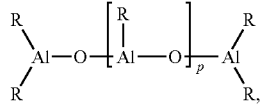  (Formula 8)

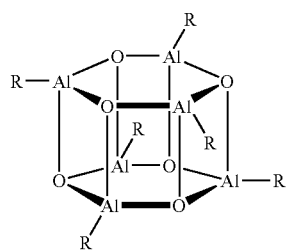  (Formula 9)

wherein radicals R in the formulas (6), (7), (8) and (9) can be identical or different and are each an alkyl group of from 1 to about 6 carbon atoms, an aryl group of from 6 to about 18 carbon atoms, benzyl or hydrogen, and p is an integer from 2 to 50.

7. The catalyst composition of claim 5 wherein the Lewis acid is a compound having formula 10:

  (Formula 10)

where
$M^2$ is B, Al or Ga, and
$X^1$, $X^2$ and $X^3$ are the same or different and each are a hydrogen atom, an alkyl group of from 1 to about 20 carbon atoms, an aryl group of from 6 to about 15 carbon atoms, alkylaryl, arylalkyl, haloalkyl or haloaryl each having from 1 to 10 carbon atoms in the alkyl radical and from 6-20 carbon atoms in the aryl radical or fluorine, chlorine, bromine or iodine.

8. The catalyst composition of claim 7 wherein the Lewis acid comprises one or more compounds selected from the group consisting of trimethylaluminum, triethylaluminum, triisobutylaluminum, tributylaluminum, trifluoroborane, triphenylborane, tris(4-fluorophenyl)borane, tris(3,5-difluorophenyl)borane, tris(4-fluoromethylphenyl)borane, tris(2,4,6-trifluorophenyl)borane, tris(penta-fluorophenyl)borane, tris(tolyl)borane, tris(3,5-dimethyl-phenyl)borane, tris(3,5-difluorophenyl)borane and tris(3,4,5-trifluorophenyl)borane.

9. The catalyst composition of claim 5 wherein the ionic compound comprises one or more compound selected from the group consisting of:
triethylammoniumtetra(phenyl)borate,
tributylammoniumtetra(phenyl)borate,
trimethylammoniumtetra(tolyl)borate,
tributylammoniumtetra(tolyl)borate,
tributylammoniurntetra(pentafluorophenyl)borate,
tributylammoniumtetra(pentaffluorophenyl) aluminate,
tripropylammoniumtetra(dimethylphenyl)borate,
tributylammoniumtetra(trifluoromethylphenyl)borate,
tributylammoniumtetra(4-fluorophenyl)borate,
N,N-dimethylcyclohexylammoniumtetrakis(pentafluorophenyl)borate,
N,N-dimethylbenzylammoniumtetrakis(pentafluorophenyl)borate N,N-dimethylaniliniumtetra(phenyl)borate,
N,N-diethylaniliniumtetra(phenyl)borate,
N,N-dimethylaniliniumtetrakis(pentafluorophenyl)borate,
N,N-dimethylaniliniumtetrakis(pentafluorophenyl)aluminate,
di(propyl)ammoniumtetrakis(pentafluorophenyl)borate,
di(cyclohexyl)ammoniumtetrakist(pentafluorophenyl)borate,
triphenylphosphoniumtetrakis(phenyl)borate,
triethylphosphoniumtetrakis(phenyl)borate,
diphenylphosphoniumtetrakis(phenyl)borate,
tri(methylphenyl)phosphoniumtetrakis(phenyl)borate,
tri(dimethylphenyl)phosphoniumtetrakis(phenyl)borate,
triphenylcarbeniumtetrakis(pentafluorophenyl)borate,
triphenylcarbeniumtetrakis(pentafluorophenyl)aluminate,
triphenylcarbeniumtetrakis(phenyl)aluminate,
ferroceniumtetrakis(pentafluorophenyl)borate and
ferroceniumtetrakis(pentafluorophenyl)aluminate.

10. The catalyst composition of claim 5 further including a particulate porous solid support.

11. The catalyst composition of claim 10 wherein the particulate porous solid support comprises at least one material selected from the group consisting of silicon dioxide, aluminum oxide, aluminosilicates, zeolites, MgO, $ZrO_2$, $TiO_2$, $B_2O_3$, CaO, ZnO, $ThO_2$, $Na_2O$, $K_2O$, $LiO_2$, Al/Si oxides, Mg/Al oxides, Al/Mg/Si oxides, $Na_2CO_3$, $K_2CO_3$, $CaCO_3$, $MgCl_2$, $Na_2SO_4$, $Al_2(SO_4)_3$, $BaSO_4$, $KNO_3$, $Mg(NO_3)_2$ and $Al(NO_3)_3$, polyethylene, polypropylene, polybutene, polystyrene, divinylbenzene-crosslinked polystyrene, polyvinyl chloride, acrylonitrile-butadiene-styrene copolymer, polyamide, polymethacrylate, polycarbonate, polyester, polyacetal and polyvinyl alcohol.

12. A method for olefin polymerization comprising contacting one or more olefins each having from 2 to about 20 carbon atoms under olefin polymerization reaction conditions with a catalyst system including a bridged metallocene component having the general formula 1,

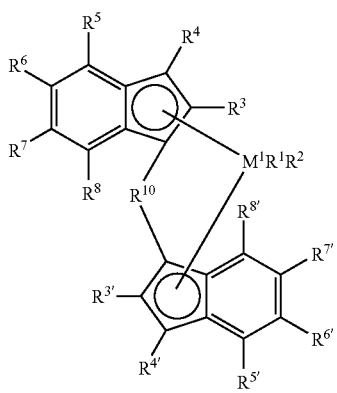

Formula 1 in which:
M¹ is a metal of the Groups 4-6 of the Periodic Table of the Elements,
$R^1$ and $R^2$ are identical or different and are each a hydrogen atom, an alkyl group of from 1 to about 10 carbon atoms, an alkoxy group of from 1 to about 10 carbon atoms, an aryl group of from 6 to about 20 carbon atoms, an aryloxy group of from 6 to about 10 carbon atoms, an alkenyl group of from 2 to about 10 carbon atoms, an OH group, a halogen atom, or a $NR_2^{32}$ group, where $R^{32}$ is an alkyl group of from 1 to about 10 carbon atoms or an aryl group of from 6 to about 14 carbon atoms and $R^1$ and $R^2$ may form one or more ring system(s),
$R^3$ and $R^{3'}$ are identical or different and are each a halogen atom, or a linear, cyclic or branched hydrocarbon group which may optionally be halogenated and/or may contain one or more hetero atoms selected from Si, B, Al, O, S, N and P, said hydrocarbon group being selected from an alkyl group of from 1 to about 20 carbon atoms, an alkylalkenyl group of from 3 to about 20 carbon atoms, an alkylaryl group of from 7 to about 40 carbon atoms, an alkylarylalkenyl group of from 9 to about 40 carbon atoms, an arylalkyl group of 7 to 20 carbon atoms, an alkoxy group of from 1 to about 10 carbon atoms, an aryl group of from 6 to about 20 carbon atoms, a heteroaryl group of 3 to about 20 carbon atoms, an aryloxy group of from 6 to about 10 carbon atoms, a silyloxy group of about 3 to 20 carbon atoms, an alkenyl group of from 2 to about 10 carbon atoms and a $NR_2^{32}$ group, where $R^{32}$ is an alkyl group of from 1 to about 10 carbon atoms or an aryl group of from 6 to about 14 carbon atoms,
$R^4$ and $R^{4'}$ are identical or different and are each a hydrogen atom, a halogen atom, or a linear, cyclic or branched hydrocarbon group which may be halogenated and/or may contain one or more hetero atoms selected from Si, B, Al, O, S, N and P, said hydrocarbon group being selected from an alkyl group of from 1 to about 20 carbon atoms, an alkylalkenyl group of from 3 to about 20 carbon atoms, an alkylaryl group of from 7 to about 40 carbon atoms, or an alkylarylalkenyl group of from 9 to about 40 carbon atoms, an arylalkyl group of 7 to 20 carbon atoms, an alkoxy group of from 1 to about 10 carbon atoms, an aryl group of from 6 to about 20 carbon atoms, a heteroaryl group of 3 to about 20 carbon atoms, an aryloxy group of from 6 to about 10 carbon atoms, a silyloxy group of about 3 to 20 carbon atoms, an alkenyl group of from 2 to about 10 carbon atoms, a halogen atom and a $NR_2^{32}$ group, where $R^{32}$ is an alkyl group of from 1 to about 10 carbon atoms or an aryl group of from 6 to about 14 carbon atoms,
$R^5$, $R^{5'}$, $R^8$ and $R^{8'}$ are identical or different and are each an aryl group of from 6 to about 40 carbon atoms, an alkylaryl group of from 7 to about 40 carbon atoms, an alkenylaryl group of from 8 to about 40 carbon atoms, a substituted or unsubstituted silylaryl group, or an (alkyl)(silyl)aryl group, and optionally may be halogenated and/or may contain one or more hetero atoms selected from Si, B, Al, O, S, N and P,
$R^6$, $R^{6'}$, $R^7$ and $R^{7'}$ are identical or different and are each a hydrogen atom, a halogen, or a linear, cyclic or branched hydrocarbon group which may optionally be halogenated and/or may contain one or more hetero atoms selected from Si, B, Al, O, S, N and P, wherein the hydrocarbon group is selected from an alkyl group of from 1 to about 20 carbon atoms, an alkylalkenyl group of from 3 to about 20 carbon atoms, an alkylaryl group of from 7 to about 40 carbon atoms, an alkylarylalkenyl group of from 9 to about 40 carbon atoms, an arylalkyl group of 7 to 20 carbon atoms, an alkoxy group of from 1 to about 10 carbon atoms, an aryl group of from 6 to about 20 carbon atoms, a heteroaryl group of 3 to about 20 carbon atoms, an aryloxy group of from 6 to about 10 carbon atoms, a silyloxy group of about 3 to 20 carbon atoms, an alkenyl group of from 2 to about 10 carbon atoms, a halogen atom and a $NR_2^{32}$ group, where $R^{32}$ is an alkyl group of from 1 to about 10 carbon atoms or an aryl group of from 6 to about 14 carbon atoms,
$R^{10}$ is a bridging group wherein $R^{10}$ is selected from:

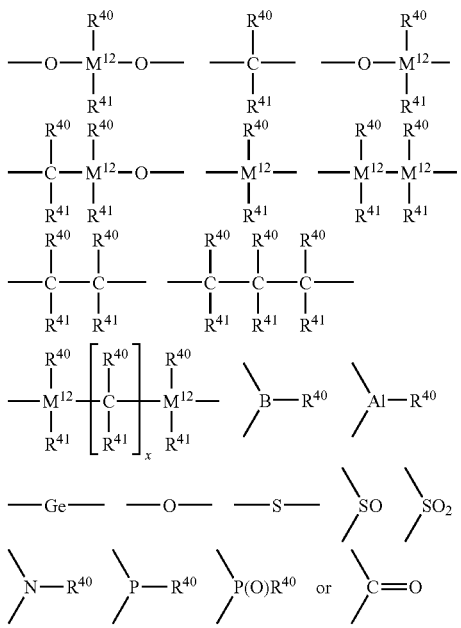

where
$R^{40}$ and $R^{41}$, even when bearing the same index, can be identical or different and are each a hydrogen atom, or a hydrocarbon group which may optionally be halogenated or which may contain hetero atoms selected from Si, B, Al, O, S, N and P, wherein the hydrocarbon group is selected from an alkyl group having from 1 to about 30 carbon atoms, an aryl group of from 6 to about 40 carbon atoms, a fluoroalkyl group of from 1 to about 10 carbon atoms, an alkoxy group of from 1 to about 10 carbon atoms, an aryloxy group of from 6 to about 10 carbon atoms, an alkenyl group of from 2 to about 10 carbon atoms, an arylalkyl group of from 7 to about 40 carbon atoms, an alkylaryl group of from 7 to about 40 carbon atoms, a substituted or unsubstituted alkylsilyl, alkyl (aryl)silyl group, an arylsilyl group and an arylalkenyl group of from 8 to about 40 carbon atoms, or wherein $R^{40}$ and $R^{41}$ together with the atoms connecting S them can form one or more cyclic systems, x is an integer from 1 to 18, $M^{12}$ is silicon, germanium or tin, and $R^{10}$ may also link two units of the formula 1 to one another.

13. The method of claim 12 wherein:

$M^1$ is a metal of the Group 4 of the Periodic Table of the Elements, $R^1$ and $R^2$ are identical or different and are each an alkyl group of from 1 to about 10 carbon atoms, an alkoxy group of from 1 to about 10 carbon atoms, an aryloxy group of from 6 to about 10 carbon atoms or a halogen atom, or $R^1$ and $R^2$ together may S form one or more ring system(s), $R^3$ and $R^{3'}$ are identical or different and are each a halogen atom or a linear, cyclic or branched hydrocarbon group which may optionally be halogenated and/or may optionally contain one or more hetero atoms selected from Si, B, Al, O, S, N and P, wherein the hydrocarbon group is selected from an alkyl group of from 1 to 0 about 10 carbon atoms, an alkylalkenyl group of from 3 to about 10 carbon atoms, an alkylaryl group of from 7 to about 20 carbon atoms, an alkylarylalkenyl group of from 9 to about 20 carbon atoms, an arylalkyl group of 7 to IS carbon atoms, an alkoxy group of from 1 to about 6 carbon atoms, an aryl group of from 6 to about 10 carbon atoms, a heteroaryl group of 3 to about 10 carbon atoms, an aryloxy 5 group of from 6 to about 10 carbon atoms, a silyloxy group of about 3 to 10 carbon atoms, an alkenyl group of from 2 to about 6 carbon atoms and a $NR_2^{32}$ group where $R^{32}$ is an alkyl group of from 1 to about 10 carbon atoms or an aryl group of from 6 to about 10 carbon atoms, $R^4$ and $R^{4'}$ are identical or different and are each a hydrogen atom, or an alkyl group of from 1 to about 20 carbon atoms which may optionally be halogenated and/or may optionally contain one or more hetero atoms selected from Si, B, Al, O, S, N and P, $R^5$, $R^{5'}$, $R^8$ and $R^{8'}$ are identical or different and are each an aryl group of from 6 to about 40 carbon atoms, an alkylaryl group of from 7 to about 40 carbon atoms, and may optionally contain one or more hetero atoms selected from B, Al, O, S, N, P, F, Cl and Br, $R^6$, $R^{6'}$, $R^7$ and $R^{7'}$ are identical or different and are each a hydrogen atom, or an alkyl group of from 1 to about 20 carbon atoms which may be halogenated and/or may contain one or more hetero atoms selected from B, Al, O, S, N and P, $R^{10}$ is $R^{40}R^{41}Si{=}$, $R^{40}R^{41}Ge{=}$, $R^{40}R^{41}C{=}$ or $-(R^{40}R^{41}C-CR^{40}R^{41})-$, where $R^{40}$ and $R^{41}$ are identical or different and are each a hydrogen atom, a hydrocarbon group of from 1 to about 40 carbon atoms selected from an alkyl group of from 1 to about 10 carbon atoms, an aryl group of from 6 to about 40 carbon atoms, an arylalkyl group of from 7 to about 14 carbon atoms and an alkylaryl group of from 7 to about 14 carbon atoms.

14. The method of claim 12 wherein $M^1$ is zirconium, $R^1$ and $R^2$ are identical and are methyl, chlorine or phenolate, $R^3$ and $R^{3'}$ are identical and are a linear, cyclic or branched hydrocarbon group selected from methyl, ethyl, n-propyl, i-propyl, cyclopropyl, n-butyl, t-butyl, t-butyl-methyl, i-butyl, s-butyl, n-pentyl, n-hexyl, n-heptyl, n-octyl, n-nonyl, n-decyl, cyclopropyl-methyl, cyclopentyl, cyclopentyl-methyl, cyclohexyl, cyclohexyl-methyl, (1-adamantyl)methyl, (2-adamantyl)methyl, benzyl, phenylethyl or phenyl-propyl, $R^4$ and $R^{4'}$ are identical and are each a hydrogen atom, $R^5$, $R^{5'}$, $R^8$ and $R^{8'}$ are identical and are each an aryl group of from 6 to about 20 carbon atoms, selected from phenyl, 1-naphtyl, 2-naphtyl, or an alkylaryl group of from 7 to about 40 carbon atoms which may optionally contain one or more hetero atoms selected from B, Al, O, S, N, P, F, Cl and Br, the alkylaryl group being selected from 4-methyl-phenyl, 4-ethyl-phenyl, 4-i-propyl-phenyl, 4-t-butyl-phenyl, 3,5-dimethylphenyl, 3,5-di-t-butyl-4-methoxy-phenyl, 2,3,4,5,6-pentafluorophenyl, $R^6$, $R^{6'}$, $R^7$ and $R^{7'}$ are identical and are each a hydrogen atom, the bridging unit $R^{10}$ is $R^{40}R^{41}Si{=}$ or $R^{40}R^{41}Ge{=}$, where $R^{40}$ and $R^{41}$ are identical or different and are methyl, ethyl, propyl, butyl, pentyl, hexyl, heptyl, octyl, nonyl, decyl, undecyl, dodecyl, cyclopentyl, cyclopentadienyl, cyclohexyl, phenyl, naphthyl, benzyl, or 3,3,3-trifluoropropyl.

15. The method of claim 12 wherein, $M^1$ is zirconium, $R^1$ and $R^2$ are identical and are methyl or chlorine, $R^3$ and $R^{3'}$ are identical and are each methyl, n-heptyl, n-octyl, n-nonyl, n-decyl, cyclohexyl-methyl, t-butyl-methyl, (1-adamantyl)methyl, (2-adamantyl)methyl, benzyl, phenethyl or phenyl-propyl, $R^4$ and $R^{4'}$ are identical and are each a hydrogen atom, $R^5$, $R^{5'}$, $R^8$ and $R^{8'}$ are identical and are each phenyl, 1-naphthyl, 2-naphtyl, 4-methyl-phenyl, 4-ethyl-phenyl, 4-i-propyl-phenyl, 44-butyl-phenyl, 3,5-dimethylphenyl, 3,5-di-t-butyl-4-methoxy-phenyl, 2,3,4,5,6-pentafluorophenyl, $R^6$, $R^{6'}$, $R^7$ and $R^{7'}$ are identical and are each a hydrogen atom the bridging unit $R^{10}$ is $R^{40}R^{41}Si{=}$ or $R^{40}R^{41}Ge{=}$, where $R^{40}$ and $R^{41}$ are identical or different and are methyl, ethyl, propyl, butyl; pentyl, hexyl, heptyl, octyl, nonyl, decyl, undecyl, dodecyl, cyclopentyl, cyclopentadienyl, cyclohexyl, phenyl, naphthyl, benzyl, or 3,3,3-trifluoropropyl.

16. The method of claim 12 wherein the catalyst system further including an aluminoxane, a Lewis acid or an ionic compound capable of converting the metallocene compound to a cationic compound.

17. The method of claim 16 wherein the aluminoxane is a compound having the general formula selected from one of formulas 6, 7, 8, or 9:

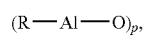
(Formula 6)

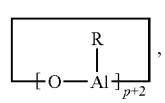
(Formula 7)

-continued

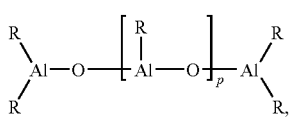
(Formula 8)

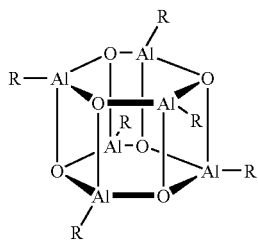
(Formula 9)

wherein radicals R in the formulas (6), (7), (8) and (9) can be identical or different and are each a an alkyl group of from 1 to about 6 carbon atoms, an aryl group of from 6 to about 18 carbon atoms, benzyl or hydrogen and p is an integer from 2 to 50.

18. The catalyst composition of claim 16 wherein the Lewis acid is a compound having formula 10:

$$M^2X^1X^2X^3 \qquad \text{(Formula 10)}$$

where $M^2$ is B, Al or Ga, and $X^1$, $X^2$ and $X^3$ are the same or different and each are a hydrogen atom, an alkyl group of from 1 to about 20 carbon atoms, an aryl group of from 6 to about 15 carbon atoms, alkylaryl, arylalkyl, haloalkyl or haloaryl each having from 1 to 10 carbon atoms in the alkyl radical and from 6-20 carbon atoms in the aryl radical or fluorine, chlorine, bromine or iodine.

19. The method of claim 18 wherein the Lewis acid comprises one or more compounds selected from the group consisting of trimethylaluminum, triethylaluminum, triisobutylaluminum, tributylaluminum, trifluoroborane, triphenylborane, tris(4-fluorophenyl)borane, tris(3,5-difluorophenyl)borane, tris(4-fluoromethylphenyl)borane, tris(2,4,6-trifluorophenyl)borane, tris(penta-fluorophenyl)borane, tris(tolyl)borane, tris(3,S-dimethyl-phenyl)borane, tris(3,5-difluorophenyl)borane and tris(3,4,S-trifluorophenyl)borane.

20. The method of claim 16 wherein the ionic compound comprises one or more compound selected from the group consisting of:
triethylammoniumtetra(phenyl)borate,
tributylammoniumtetra(phenyl)borate,
trimethylammoniumtetra(tolyl)borate,
tributylammoniumtetra(tolyl)borate,
tributylammoniumtetra(pentafluorophenyl)borate,
tributylammoniurntetra(pentaffluorophenyl) aluminate,
tripropylammoniumtetra(dimethylphenyl)borate,
tributylammoniumtetra(trifluoromethylphenyl)borate,
tributylammoniumtetra(4-fluorophenyl)borate,
N,N-dimethylcyclohexylammoniumtetrakis(pentafluorophenyl)borate,
N,N-dimethylbenzylammoniumtetrakis(pentafluorophenyl)borate
N,N-dimethylaniliniumtetra(phenyl)borate,
N,N-diethylaniliniumtetra(phenyl)borate,
N,N-dimethylaniliniumtetrakis(pentafluorophenyl)borate,
N,N-dimethylaniliniumtetrakis(pentafluorophenyl)aluminate,
di(propyl)ammoniurntetrakis(pentafluorophenyl)borate,
di(cyclohexyl)ammoniumtetrakist(pentafluorophenyl)borate,
triphenylphosphoniumtetrakis(phenyl)borate,
triethylphosphoniumtetrakis(phenyl)borate,
diphenylphosphoniumtetrakis(phenyl)borate,
tri(methylphenyl)phosphoniuintetrakis(phenyl)borate,
tri(dimethylphenyl)phosphoninmtetrakis(phenyl)borate,
triphenylcarbeniumtetrakis(pentafluorophenyl)borate,
triphenylcarbeniumtetrakis(pentafluorophenyl)aluminate,
triphenylcarbeniumtetrakis(phenyl)aluminate,
ferroceniumtetrakis(pentailuorophenyl)borate and
ferroceniumtetrakis(pentafluorophenyl)aluminate.

21. The method of claim 12 wherein the one or more olefins include propylene and/or ethylene.

22. The method of claim 21 wherein the one or more olefins further include one or more of 1-butene, hexene, 1,4-butadiene, norbornadiene, ethylidenenorbornene of ethylnorbornadiene.

23. A method for preparing a bridged metallocene comprising:

a) providing a compound having the formula 1a

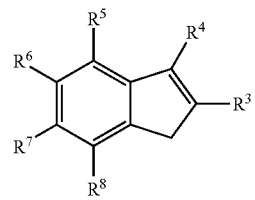

Formula 1a b) reacting the compound of formula 1a with a base under reaction conditions sufficient to achieve deprotonation of the compound having formula 1 a;

c) reacting the deprotonated compound of step (b) with a compound having the formula $M^{12}R^{40}R^{41}X_2$ wherein $M^{12}$ is silicon, germanium or tin, $R^{40}$ and $R^{41}$, even when bearing the same index, can be identical or different and are each a hydrogen atom, or a hydrocarbon group which may optionally be halogenated or which may contain hetero atoms selected from Si, B, Al, O, S, N and P, wherein the hydrocarbon group is selected from an alkyl group having from 1 to about 30 carbon atoms, an aryl group of from 6 to about 40 carbon atoms, a fluoroalkyl group of from 1 to about 10 carbon atoms, an alkoxy group of from 1 to about 10 carbon atoms, an aryloxy group of from 6 to about 10 carbon atoms, an alkenyl group of from 2 to about 10 carbon atoms, an arylalkyl group of from 7 to about 40 carbon atoms, an alkylaryl group of from 7 to about 40 carbon atoms, a substituted or unsubstituted alkylsilyl, alkyl(aryl)silyl group, an arylsilyl group and an arylalkenyl group of from 8 to about 40 carbon atoms, or wherein $R^{40}$ and $R^{41}$ together with the atoms connecting them can form one or more cyclic systems, and X is a halogen or another leaving group like triflate, tosylate, or mesylate, to provide a compound having formula 1b Formula 1b

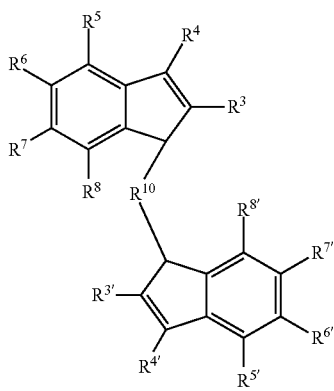

wherein

R³ and R³' are identical or different and are each a halogen atom, or a linear, cyclic or branched hydrocarbon group which may optionally be halogenated and/or may contain one or more hetero atoms selected from Si, B, Al, O, S, N and P, said hydrocarbon group being selected from an alkyl group of from 1 to about 20 carbon atoms, an alkylalkenyl group of from 3 to about 20 carbon atoms, an alkylaryl group of from 7 to about 40 carbon atoms, an alkylarylalkenyl group of from 9 to about 40 carbon atoms, an arylalkyl group of 7 to 20 carbon atoms, an alkoxy group of from 1 to about 10 carbon atoms, an aryl group of from 6 to about 20 carbon atoms, heteroaryl group of 3 to about 20 carbon atoms, an aryloxy group of from 6 to about 10 carbon atoms, a silyloxy group of about 3 to 20 carbon atoms, an alkenyl group of from 2 to about 10 carbon atoms and a $NR_2^{32}$ group, where $R^{32}$ is an alkyl group of from 1 to about 10 carbon atoms or an aryl group of from 6 to about 14 carbon atoms, R⁴ and R⁴' are identical or different and are each a hydrogen atom, a halogen atom, or a linear, cyclic or branched hydrocarbon group which may be halogenated and/or may contain one or more hetero atoms selected from Si, B, Al, O, S, N and P, said hydrocarbon group being selected from an alkyl group of from 1 to about 20 carbon atoms, an alkylalkenyl group of from 3 to about 20 carbon atoms, an alkylaryl group of from 7 to about 40 carbon atoms, an alkylarylalkenyl group of from 9 to about 40 carbon atoms, an arylalkyl group of 7 to 20 carbon atoms, an alkoxy group of from 1 to about 10 carbon atoms, an aryl group of from 6 to about 20 carbon atoms, a heteroaryl group of 3 to about 20 carbon atoms, an aryloxy group of from 6 to about 10 carbon atoms, a silyloxy group of about 3 to 20 carbon atoms, an alkenyl group of from 2 to about 10 carbon atoms, a halogen atom and a $NR_2$ group, where R is an alkyl group of from 1 to about 10 carbon atoms or an aryl group of from 6 to about 14 carbon atoms, R⁵, R⁵', R⁸ and R⁸' are identical or different and are each an aryl group of from 6 to about 40 carbon atoms, an alkylaryl group of from 7 to about 40 carbon atoms, an alkenylaryl group of from 8 to about 40 carbon atoms, a substituted or unsubstituted silylaryl group, or an (alkyl)(silyl)aryl group, and optionally may be halogenated and/or may contain one or more hetero atoms selected from Si, B, Al, O, S, N and P, R⁶, R⁶', R⁷ and R⁷' are identical or different and are each a hydrogen atom, a halogen, or a linear, cyclic or branched hydrocarbon group which may optionally be halogenated and/or may contain one or more hetero atoms selected from Si, B, Al, O, S, N and P, wherein the hydrocarbon group is selected from an alkyl group of from 1 to about 20 carbon atoms, an alkylalkenyl group of from 3 to about 20 carbon atoms, an alkylaryl group of from 7 to about 40 carbon atoms, an alkylarylalkenyl group of from 9 to about 40 carbon atoms, an arylalkyl group of 7 to 20 carbon atoms, an alkoxy group of from 1 to about 10 carbon atoms, an aryl group of from 6 to about 20 carbon atoms, a heteroaryl group of 3 to about 20 carbon atoms, an aryloxy group of from 6 to about 10 carbon atoms, a silyloxy group of about 3 to 20 carbon atoms, an alkenyl group of from 2 to about 10 carbon atoms, a halogen atom and a $NR_2^{32}$ group, where $R^{32}$ is an alkyl group of from 1 to about 10 carbon atoms or an aryl group of from 6 to about 0.14 carbon atoms, $R^{10}$ is a bridging group wherein $R^{10}$ is selected from:

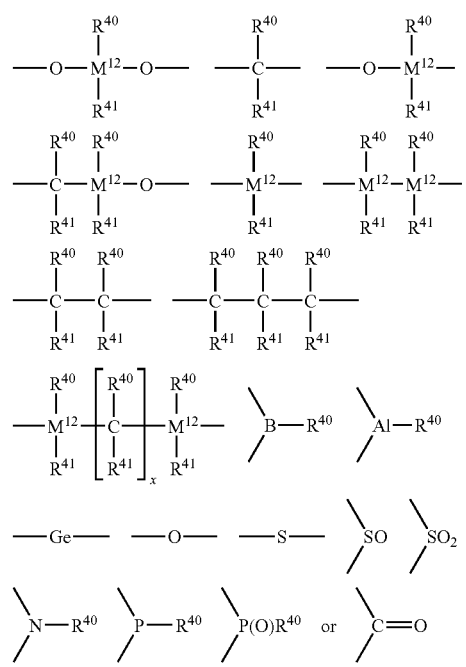

where $R^{40}$ and $R^{41}$, even when bearing the same index, can be identical or different and are each a hydrogen atom, or a hydrocarbon group which may optionally be halogenated or which may contain hetero atoms selected from Si, B, Al, O, S, N and P, wherein the hydrocarbon group is selected from an alkyl group having from 1 to about 30 carbon atoms, an aryl group of from 6 to about 40 carbon atoms, a fluoroalkyl group of from 1 to about 10 carbon atoms, an alkoxy group of from 1 to about 10 carbon atoms, an aryloxy group of from 6 to about 10 carbon atoms, an alkenyl group of from 2 to about 10 carbon atoms, an arylalkyl group of from 7 to about 40 carbon atoms, an alkylaryl group of from 7 to about 40 carbon atoms, a substituted or unsubstituted alkylsilyl, alkyl(aryl)silyl group, an arylsilyl group and an arylalkenyl group of from 8 to about 40 carbon atoms, or wherein $R^{40}$ and $R^{41}$ together with the atoms connecting them can form one or more cyclic systems, x is an integer from 1 to 18, $M^{12}$ is silicon, germanium or tin, and $R^{10}$ may also link two units of the formula 1 to one another;

d) reacting the compound of formula 1b with a base under conditions sufficient to achieve double deprotonation of the compound of formula 1b; and e) reacting the double deprotonated compound from step (d) with a compound having the formula $M^1Cl_4$ wherein $M^1$ is zirconium, titanium or hafnium, to provide a bridged metallocene compound of substantially 100% pure racemic isomer as synthesized.

24. The method of claim 23 wherein the base is n-butyl lithium.

25. The method of claim 23 wherein the steps (b) and (d) of deprotonation are carried out at a temperature of from about −70° C. to about 80° C.

26. The method of claim 23 wherein $M^{12}$ is silicon and $M^1$ is zirconium.

27. The catalyst composition of claim 1, wherein the metallocene compound having formula 1 is selected from the group consisting of Dimethylsilanediylbis(2-methyl-4,7-diphenyl-indenyl)zirconium dichloride;
Dimethylsilanediylbis(2-ethyl-4,7-diphenyl-indenyl)zirconium dichloride,
Dimethylsilanediylbis(2-n-propyl-4,7-diphenyl-indenyl)zirconium dichloride,
Dimethylsilanediylbis(2-i-propyl-4,7-diphenyl-indenyl)zirconium dichloride,
Dimethylsilanediylbis(2-n-butyl-4,7-diphenyl-indenyl)zirconium dichloride,
Dimethylsilanediylbis(2-s-butyl-4,7-diphenyl-indenyl)zirconium dichloride,
Dimethylsilanediylbis(2-t-butyl-4,7-diphenyl-indenyl)zirconium dichloride,
Dimethylsilanediylbis(2-n-pentyl-4,7-diphenyl-indenyl)zirconium dichloride,
Dimethylsilanediylbis(2-n-hexyl-4,7-diphenyl-indenyl)zirconium dichloride,
Dimethylsilanediylbis(2-n-heptyl-4,7-diphenyl-indenyl)zirconium dichloride,
Dimethylsilanediylbis(2-cyclopropylmethyl-4,7-diphenyl-indenyl)zirconium dichloride,
Dimethylsilanediylbis(2-cyclobutylmethyl-4,7-diphenyl-indenyl)zirconium dichloride,
Dimethylsilanediylbis(2-cyclopentylmethyl-4,7-diphenyl-indenyl)zirconium dichloride,
Dimethylsilanediylbis(2-cyclohexylmethyl-4,7-diphenyl-indenyl)zirconium dichloride,
Dimethylsilanediylbis(2-cycloheptylmethyl-4,7-diphenyl-indenyl)zirconium dichloride,
Dimethylsilanediylbis(2-(1-adamantyl)methyl-4,7-diphenyl-indenyl)zirconium dichloride,
Dimethylsilanediylbis(2-t-butyl-methyl-4,7-diphenyl-indenyl)zirconium dichloride,
Dimethylsilanediylbis(2,4,7-triphenyl-indenyl)zirconium dichloride,
Dimethylsilanediylbis(2-benzyl-4,7-diphenyl-indenyl)zirconium dichloride,
Dimethylsilanediylbis(2-phenethyl-4,7-diphenyl-indenyl)zirconium dichloride,
Dimethylsilanediylbis(2-phenylpropyl-4,7-diphenyl-indenyl)zirconium dichloride,
Dimethylsilanediylbis(2-phenylbutyl-4,7-diphenyl-indenyl)zirconium dichloride,
Dimethylsilanediylbis(2-methyl-4,7-bis-(4-methyl-phenyl)-indenyl)zirconium dichloride,
Dimethylsilanediylbis(2-ethyl-4,7-bis-(4-methyl-phenyl)-indenyl)zirconium dichloride,
Dimethylsilanediylbis(2-n-propyl-4,7-bis-(4-methyl-phenyl)-indenyl)zirconium dichloride,
Dimethylsilanediylbis(2-i-propyl-4,7-bis-(4-methyl-phenyl)-indenyl)zirconium dichloride,
Dimethylsilanediylbis(2-n-butyl-4,7-bis-(4-methyl-phenyl)-indenyl)zirconium dichloride,
Dimethylsilanediylbis(2-s-butyl-4,7-bis-(4-methyl-phenyl)-indenyl)zirconium dichloride,
Dimethylsilanediylbis(2-t-butyl-4,7-bis-(4-methyl-phenyl)-indenyl)zirconium dichloride,
Dimethylsilanediylbis(2-n-pentyl-4,7-bis-(4-methyl-phenyl)-indenyl)zirconium dichloride,
Dimethylsilanediylbis(2-n-hexyl-4,7-bis-(4-methyl-phenyl)-indenyl)zirconium dichloride,
Dimethylsilanediylbis(2-n-heptyl-4,7-bis-(4-methyl-phenyl)-indenyl)zirconium dichloride,
Dimethylsilanediylbis(2-cyclopropylmethyl-4,7-bis-(4-methyl-phenyl)-indenyl)zirconium dichloride,
Dimethylsilanediylbis(2-cyclobutylmethyl-4,7-bis-(4-methyl-phenyl)-indenyl)zirconium dichloride,
Dimethylsilanediylbis(2-cyclopentylmethyl-4,7-bis-(4-methyl-phenyl)-indenyl)zirconium dichloride,
Dimethylsilanediylbis(2-cyclohexylmethyl-4,7-bis-(4-methyl-phenyl)-indenyl)zirconium dichloride,
Dimethylsilanediylbis(2-cycloheptylmethyl-4,7-bis-(4-methyl-phenyl)-indenyl)zirconium dichloride,
Dimethylsilanediylbis(2-(1-adamantyl)methyl-4,7-bis-(4-methyl-phenyl)-indenyl)zirconium dichloride,
Dimethylsilanediylbis(2-t-butyl-methyl-4,7-bis-(4-methyl-phenyl)-indenyl)zirconium dichloride,
Dimethylsilanediylbis(2-(1-furyl)-4,7-bis-(4-methyl-phenyl)-indenyl)zirconium dichloride,
Dimethylsilanediylbis(2-benzyl-4,7-bis-(4-methyl-phenyl)-indenyl)zirconium dichloride,
Dimethylsilanediylbis(2-phenethyl-4,7-bis-(4-methyl-phenyl)-indenyl)zirconium dichloride,
Dimethylsilanediylbis(2-phenylpropyl-4,7-bis-(4-methyl-phenyl)-indenyl)zirconium dichloride,
Dimethylsilanediylbis(2-phenylbutyl-4,7-bis-(4-methyl-phenyl)-indenyl)zirconium dichloride,
Dimethylsilanediylbis(2-methyl-4,7-bis-(4-t-butyl-phenyl)-indenyl)zirconium dichloride,
Dimethylsilanediylbis(2-ethyl-4,7-bis-(4-t-butyl-phenyl)-indenyl)zirconium dichloride,
Dimethylsilanediylbis(2-n-propyl-4,7-bis-(4-t-butyl-phenyl)-indenyl)zirconium dichloride,
Dimethylsilanediylbis(2-i-propyl-4,7-bis-(4-t-butyl-phenyl)-indenyl)zirconium dichloride,
Dimethylsilanediylbis(2-n-butyl-4,7-bis-(4-t-butyl-phenyl)-indenyl)zirconium dichloride,
Dimethylsilanediylbis(2-s-butyl-4,7-bis-(4-t-butyl-phenyl)-indenyl)zirconium dichloride,
Dimethylsilanediylbis(2-t-butyl-4,7-bis-(4-t-butyl-phenyl)-indenyl)zirconium dichloride,
Dimethylsilanediylbis(2-n-pentyl-4,7-bis-(4-t-butyl-phenyl)-indenyl)zirconium dichloride,
Dimethylsilanediylbis(2-n-hexyl-4,7-bis-(4-t-butyl-phenyl)-indenyl)zirconium dichloride,
Dimethylsilanediylbis(2-n-heptyl-4,7-bis-(4-t-butyl-phenyl)-indenyl)zirconium dichloride,
Dimethylsilanediylbis(2-cyclopropylmethyl-4,7-bis-(4-t-butyl-phenyl)-indenyl)zirconium dichloride,
Dimethylsilanediylbis(2-cyclobutylmethyl-4,7-bis-(4-t-butyl-phenyl)-indenyl)zirconium dichloride, Dimethylsilanediylbis(2-cyclopentylmethyl-4,7-bis-(4-t-butyl-phenyl)-indenyl)zirconium dichloride,
Dimethylsilanediylbis(2-cyclohexylmethyl-4,7-bis-(4-t-butyl-phenyl)-indenyl)zirconium dichloride,
Dimethylsilanediylbis(2-cycloheptylmethyl-4,7-bis-(4-t-butyl-phenyl)-indenyl)zirconium dichloride,
Dimethylsilanediylbis(2-(1-adamantyl)methyl-4,7-bis-(4-t-butyl-phenyl)-indenyl)zirconium dichloride,
Dimethylsilanediylbis(2-t-butyl-methyl-4,7-bis-(4-t-butyl-phenyl)-indenyl)zirconium dichloride,
Dimethylsilanediylbis(2-(1-furyl)-4,7-bis-(4-t-butyl-phenyl)-indenyl)zirconium dichloride,
Dimethylsilanediylbis(2-benzyl-4,7-bis-(4-t-butyl-phenyl)-indenyl)zirconium dichloride,
Dimethylsilanediylbis(2-phenethyl-4,7-bis-(4-t-butyl-phenyl)-indenyl)zirconium dichloride,
Dimethylsilanediylbis(2-phenylpropyl-4,7-bis-(4-t-butyl-phenyl)-indenyl)zirconium dichloride,
Dimethylsilanediylbis(2-phenylbutyl-4,7-bis-(4-t-butyl-phenyl)-indenyl)zirconium dichloride,
Dimethylsilanediylbis(2-methyl-4,7-bis-(3,5-dimethyl-phenyl)-indenyl)zirconium dichloride,
Dimethylsilanediylbis(2-ethyl-4,7-bis-(3,5-dimethyl-phenyl)-indenyl)zirconium dichloride,
Dimethylsilanediylbis(2-n-propyl-4,7-bis-(3,5-dimethyl-phenyl)-indenyl)zirconium dichloride,
Dimethylsilanediylbis(2-i-propyl-4,7-bis-(3,5-dimethyl-phenyl)-indenyl)zirconium dichloride,
Dimethylsilanediylbis(2-n-butyl-4,7-bis-(3,5-dimethyl-phenyl)-indenyl)zirconium dichloride,
Dimethylsilanediylbis(2-s-butyl-4,7-bis-(3,5-dimethyl-phenyl)-indenyl)zirconium dichloride,
Dimethylsilanediylbis(2-t-butyl-4,7-bis-(3,5-dimethyl-phenyl)-indenyl)zirconium dichloride,
Dimethylsilanediylbis(2-n-pentyl-4,7-bis-(3,5-dimethyl-phenyl)-indenyl)zirconium dichloride,
Dimethylsilanediylbis(2-n-hexyl-4,7-bis-(3,5-dimethyl-phenyl)-indenyl)zirconium dichloride,
Dimethylsilanediylbis(2-n-heptyl-4,7-bis-(3,5-dimethyl-phenyl)-indenyl)zirconium dichloride,
Dimethylsilanediylbis(2-cyclopropylmethyl-4,7-bis-(3,5-dimethyl-phenyl)-indenyl)zirconium dichloride,
Dimethylsilanediylbis(2-cyclobutylmethyl-4,7-bis-(3,5-dimethyl-phenyl)-indenyl)zirconium dichloride,
Dimethylsilanediylbis(2-cyclopentylmethyl-4,7-bis-(3,5-dimethyl-phenyl)-indenyl)zirconium dichloride,
Dimethylsilanediylbis(2-cyclohexylmethyl-4,7-bis-(3,5-dimethyl-phenyl)-indenyl)zirconium dichloride,
Dimethylsilanediylbis(2-cycloheptylmethyl-4,7-bis-(3,5-dimethyl-phenyl)-indenyl)zirconium dichloride,
Dimethylsilanediylbis(2-(1-adamantyl)methyl-4,7-bis-(3,5-dimethyl-phenyl)-indenyl)zirconium dichloride,
Dimethylsilanediylbis(2-t-butyl-methyl-4,7-bis-(3,5-dimethyl-phenyl)-indenyl)zirconium dichloride,
Dimethylsilanediylbis(2-(1-furyl)-4,7-bis-(3,5-dimethyl-phenyl)-indenyl)zirconium dichloride,
Dimethylsilanediylbis(2-benzyl-4,7-bis-(3,5-dimethyl-phenyl)-indenyl)zirconium dichloride,
Dimethylsilanediylbis(2-phenethyl-4,7-bis-(3,5-dimethyl-phenyl)-indenyl)zirconium dichloride,
Dimethylsilanediylbis(2-phenylpropyl-4,7-bis-(3,5-dimethyl-phenyl)-indenyl)zirconium dichloride,
Dimethylsilanediylbis(2-phenylbutyl-4,7-bis-(3,5-dimethyl-phenyl)-indenyl)zirconium dichloride,
Dimethylsilanediylbis(2-methyl-4,7-bis-(1-naphthyl)-indenyl)zirconium dichloride,
Dimethylsilanediylbis(2-ethyl-4,7-bis-(1-naphthyl)-indenyl)zirconium dichloride,
Dimethylsilanediylbis(2-n-propyl-4,7-bis-(1-naphthyl)-indenyl)zirconium dichloride,
Dimethylsilanediylbis(2-i-propyl-4,7-bis-(1-naphthyl)-indenyl)zirconium dichloride,
Dimethylsilanediylbis(2-n-butyl-4,7-bis-(1-naphthyl)-indenyl)zirconium dichloride,
Dimethylsilanediylbis(2-s-butyl-4,7-bis-(1-naphthyl)-indenyl)zirconium dichloride,
Dimethylsilanediylbis(2-t-butyl-4,7-bis-(1-naphthyl)-indenyl)zirconium dichloride,
Dimethylsilanediylbis(2-n-pentyl-4,7-bis-(1-naphthyl)-indenyl)zirconium dichloride,
Dimethylsilanediylbis(2-n-hexyl-4,7-bis-(1-naphthyl)-indenyl)zirconium dichloride,
Dimethylsilanediylbis(2-n-heptyl-4,7-bis-(1-naphthyl)-indenyl)zirconium dichloride,
Dimethylsilanediylbis(2-cyclopropylmethyl-4,7-bis-(1-naphthyl)-indenyl)zirconium dichloride,
Dimethylsilanediylbis(2-cyclobutylmethyl-4,7-bis-(1-naphthyl)-indenyl)zirconium dichloride,
Dimethylsilanediylbis(2-cyclopentylmethyl-4,7-bis-(1-naphthyl)-indenyl)zirconium dichloride,
Dimethylsilanediylbis(2-cyclohexylmethyl-4,7-bis-(1-naphthyl)-indenyl)zirconium dichloride,
Dimethylsilanediylbis(2-cycloheptylmethyl-4,7-bis-(1-naphthyl)-indenyl)zirconium dichloride,
Dimethylsilanediylbis(2-(1-adamantyl)methyl-4,7-bis-(1-naphthyl)-indenyl)zirconium dichloride,
Dimethylsilanediylbis(2-t-butyl-methyl-4,7-bis-(1-naphthyl)-indenyl)zirconium dichloride,
Dimethylsilanediylbis(2-(1-ftiryl)-4,7-bis-(1-naphthyl)-indenyl)zirconium dichloride,
Dimethylsilanediylbis(2-benzyl-4,7-bis-(1-naphthyl)-indenyl)zirconium dichloride,
Dimethylsilanediylbis(2-phenethyl-4,7-bis-(1-naphthyl)-indenyl)zirconium dichloride,
Dimethylsilanediylbis(2-phenylpropyl-4,7-bis-(1-naphthyl)-indenyl)zirconium dichloride,
Dimethylsilanediylbis(2-phenylbutyl-4,7-bis-(1-naphthyl)-indenyl)zirconium dichloride,
Dimethylsilanediylbis(2-methyl-4,7-bis-(9-anthracenyl)-indenyl)zirconium dichloride,
Dimethylsilanediylbis(2-ethyl-4,7-bis-(9-anthracenyl)-indenyl)zirconium dichloride,
Dimethylsilanediylbis(2-n-propyl-4,7-bis-(9-anthracenyl)-indenyl)zirconium dichloride,
Dimethylsilanediylbis(2-i-propyl-4,7-bis-(9-anthracenyl)-indenyl)zirconium dichloride,
Dimethylsilanediylbis(2-n-butyl-4,7-bis-(9-anthracenyl)-indenyl)zirconium dichloride,
Dimethylsilanediylbis(2-s-butyl-4,7-bis-(9-anthracenyl)-indenyl)zirconium dichloride,
Dimethylsilanediylbis(2-t-butyl-4,7-bis-(9-anthracenyl)-indenyl)zirconium dichloride,
Dimethylsilanediylbis(2-n-pentyl-4,7-bis-(9-anthracenyl)-indenyl)zirconium dichloride,
Dimethylsilanediylbis(2-n-hexyl-4,7-bis-(9-anthracenyl)-indenyl)zirconium dichloride,
Dimethylsilanediylbis(2-n-heptyl-4,7-bis-(9-anthracenyl)-indenyl)zirconium dichloride,
Dimethylsilanediylbis(2-cyclopropylmethyl-4,7-bis-(9-anthracenyl)-indenyl)zirconium dichloride,
Dimethylsilanediylbis(2-cyclobutylmethyl-4,7-bis-(9-anthracenyl)-indenyl)zirconium dichloride, Dimethylsilanediylbis(2-cyclopentylmethyl-4,7-bis-(9-anthracenyl)-indenyl)zirconium dichloride,
Dimethylsilanediylbis(2-cyclohexylmethyl-4,7-bis-(9-anthracenyl)-indenyl)zirconium dichloride,
Dimethylsilanediylbis(2-cycloheptylmethyl-4,7-bis-(9-anthracenyl)-indenyl)zirconium dichloride,
Dimethylsilanediylbis(2-(1-adamantyl)methyl-4,7-bis-(9-anthracenyl)-indenyl)zirconium dichloride,
Dimethylsilanediylbis(2-t-butyl-methyl-4,7-bis-(9-anthracenyl)-indenyl)zirconium dichloride,
Dimethylsilanediylbis(2-(1-furyl)-4,7-bis-(9-anthracenyl)-indenyl)zirconium dichloride,
Dimethylsilanediylbis(2-benzyl-4,7-bis-(9-anthracenyl)-indenyl)zirconium dichloride,
Dimethylsilanediylbis(2-phenethyl-4,7-bis-(9-anthracenyl)-indenyl)zirconium dichloride,
Dimethylsilanediylbis(2-phenylpropyl-4,7-bis-(9-anthracenyl)-indenyl)zirconium dichloride and Dimethylsilanediylbis(2-phenylbutyl-4,7-bis-(9-anthracenyl)-indenyl)zirconium dichloride.

* * * * *